US008134046B2

(12) United States Patent
Cirpus et al.

(10) Patent No.: US 8,134,046 B2
(45) Date of Patent: Mar. 13, 2012

(54) METHOD FOR PRODUCING ARACHIDONIC ACID AND/OR EICOSAPENTAENOIC ACID IN USEFUL TRANSGENIC PLANTS

(75) Inventors: Petra Cirpus, Waldsee (DE); Jörg Bauer, Limburgerhof (DE); Xiao Qiu, Saskatoon (CA); Guohai Wu, Saskatoon (CA); Nagamani Datla, Saskatoon (CA); Martin Truksa, Edmonton (CA)

(73) Assignee: BASF Plant Science GmbH (DE)

( * ) Notice: Subject to any disclaimer, the term of this patent is extended or adjusted under 35 U.S.C. 154(b) by 1001 days.

(21) Appl. No.: 11/990,244

(22) PCT Filed: Aug. 1, 2006

(86) PCT No.: PCT/EP2006/064922
§ 371 (c)(1),
(2), (4) Date: Feb. 8, 2008

(87) PCT Pub. No.: WO2007/017419
PCT Pub. Date: Feb. 15, 2007

(65) Prior Publication Data
US 2009/0234006 A1    Sep. 17, 2009

(30) Foreign Application Priority Data

Aug. 9, 2005  (DE) .......................... 10 2005 038 036

(51) Int. Cl.
*C12N 15/82* (2006.01)
*A01H 5/00* (2006.01)

(52) U.S. Cl. ........................................ 800/281; 800/298
(58) Field of Classification Search .......................... None
See application file for complete search history.

(56) References Cited

U.S. PATENT DOCUMENTS

| 5,614,393 | A | 3/1997 | Thomas et al. |
| 6,043,411 | A | 3/2000 | Nishizawa et al. |
| 2002/0156254 | A1* | 10/2002 | Qiu et al. ............... 536/23.1 |
| 2004/0172682 | A1* | 9/2004 | Kinney et al. ............ 800/281 |
| 2007/0028326 | A1 | 2/2007 | Cirpus et al. |

FOREIGN PATENT DOCUMENTS

| CA | 2 399 349 A1 | 8/2001 |
| CA | 2 533 613 A1 | 2/2005 |
| CA | 2 559 360 A1 | 9/2005 |
| CA | 2 600 286 A1 | 9/2006 |
| EP | 0 550 162 A1 | 7/1993 |
| EP | 0 794 250 A1 | 9/1997 |
| WO | WO-91/13972 A1 | 9/1991 |
| WO | WO-93/06712 A1 | 4/1993 |
| WO | WO-93/11245 A1 | 6/1993 |
| WO | WO-94/11516 A1 | 5/1994 |
| WO | WO-94/18337 A1 | 8/1994 |
| WO | WO-95/18222 A1 | 7/1995 |
| WO | WO-96/21022 A2 | 7/1996 |
| WO | WO-97/21340 A1 | 6/1997 |
| WO | WO-97/30582 A1 | 8/1997 |
| WO | WO-98/46763 A1 | 10/1998 |
| WO | WO-98/46764 A1 | 10/1998 |
| WO | WO-98/46765 A1 | 10/1998 |
| WO | WO-98/46776 A2 | 10/1998 |
| WO | WO-99/27111 A1 | 6/1999 |
| WO | WO-99/64616 A2 | 12/1999 |
| WO | WO-00/12720 A2 | 3/2000 |
| WO | WO-00/21557 A1 | 4/2000 |
| WO | WO-01/59128 A2 | 8/2001 |
| WO | WO-02/08401 A2 | 1/2002 |
| WO | WO-02/077213 A2 | 10/2002 |
| WO | WO-03/093482 A2 | 11/2003 |
| WO | WO-2005/012316 A2 | 2/2005 |
| WO | WO-2005/083093 A2 | 9/2005 |
| WO | WO-2005/118814 A2 | 12/2005 |
| WO | WO-2006/100241 A2 | 9/2006 |

OTHER PUBLICATIONS

Bork et al, TIG 12(10): 425-427, Oct. 1996.*
Brenner, SE, TIG 15(4): 132-133, Apr. 1999.*
Broun et al, Science 282: 1315-1317, Nov. 13, 1998.*
Van de Loo et al, PNAS, USA 92: 6743-6747, Jul. 1995.*
Doerks et al, TIG 14(6): 248-250, Jun. 1998.*
Wu, G., et al., "Stepwise engineering to produce high yields of very long-chain polyunsaturated fatty acids in plants", Nature Biotechnology, 2005, vol. 23, No. 8, pp. 1013-1017.
Abbadi, A., et al., "Biosynthesis of very-long-chain polyunsaturated fatty acids in transgenic oilseeds: contraints on their accumulation", The Plant Cell, 2004, vol. 16, pp. 2734-2748.
Drexler, H., et al., "Metabolic engineering of fatty acids for breeding of new oilseed crops: strategies, problems and first results", J. Plant Physiol., 2003, vol. 160, pp. 779-802.
"Delta-6 fatty acid desaturase", Database UniProtKB/TrEMBL, Accession No. Q944W4, Dec. 1, 2001.
Qiu, X., et al., "Identification of a Δ4 fatty acid desaturase from *Thraustochytrium* sp. involved in the biosynthesis of docosahexanoic acid by heterologous expression in *Saccharomyces cerevisiae* and *Brassica juncea*", J. Biol. Chem., 2001, vol. 276, No. 34, pp. 31561-31566.
"Polyunsaturated fatty acid elongase 1", Database UniProtKB/TrEMBL, Accession No. Q5SE76, Dec. 1, 2004.

(Continued)

*Primary Examiner* — Elizabeth McElwain
(74) *Attorney, Agent, or Firm* — Connolly Bove Lodge & Hutz LLP

(57) ABSTRACT

The present invention relates to a process for producing arachidonic acid and/or eicosapentaenoic acid in transgenic useful plants by introducing into the plant nucleic acids coding for polypeptides having Δ6-desaturase, Δ6-elongase or Δ5-desaturase activity. Furthermore, a gene coding for an ω3-desaturase is advantageously expressed in said useful plants. In another advantageous embodiment of the process, further nucleic acid sequences coding for polypeptides of fatty acid or lipid metabolism biosynthesis may be expressed in the plants. Particularly advantageous nucleic acid sequences here are those coding for a Δ8-desaturase, Δ12-desaturase, Δ15-desaturase, Δ4-desaturase, Δ9-elongase and/or Δ5-elongase activity.
The invention further relates to the use of the oils, lipids and/or fatty acids produced in the process according to the invention in feedstuffs or foodstuffs, cosmetics or pharmaceuticals.

20 Claims, 1 Drawing Sheet

OTHER PUBLICATIONS

Truska, M., et al., "Metabolic engineering of plants to produce very long-chain polyunsaturated fatty acids", Transgenic Research, 2006, vol. 15, No. 2, pp. 131-137.

Stukey, J. E., et al., "The OLE1 gene of *Saccharomyces cerevisiae* encodes the Δ9 fatty acid desaturase and can be functionally replaced by the rat stearoyl-CoA desaturase gene", J. Biol. Chem., 1990, vol. 265, No. 33, pp. 20144-20149.

Huang, Y.-S., et al., "Cloning of Δ12 and Δ6-desaturases from *Mortierella* alpina and recombinant production of γ-linolenic acid in *Saccharomyces cerevisiae*", Lipids, 1999, vol. 34, No. 7, pp. 649-659.

Tocher, D. R., et al., "Recent advances in the biochemistry and molecular biology of fatty acyl desaturases", Prog. Lipid Res., 1998, vol. 37, No. 2/3, pp. 73-117.

Domergue, F., et al., "Cloning and functional characterization of *Phaeodactylum tricornutum* front-end desaturases involved in eicosapentaenoic acid biosynthesis", Eur. J. Biochem., 2002, vol. 269, pp. 4105-4113.

Hong, H., et al., "High-Level Production of γ-Linolenic Acid in *Brassica juncea* Using a Δ6 Desaturase from *Pythium irregulare*", Plant Physiology, vol. 129, (2002), pp. 354-362.

Meyer, A., et al., "Novel Fatty Acid Elongases and their use for the Reconstitution of Docosahexaenoic Acid Biosynthesis", Journal of Lipid Research, vol. 45, (2004), pp. 1899-1909.

Truksa, M., et al., "Metabolic Engineering of Plants to Produce Very Long-Chain Polyunsaturated Fatty Acids", Transgenic Research, vol. 15, (2006), pp. 131-137.

\* cited by examiner

Figure 1: Vectors used for plant transformation.
  A) pGPTV-D6D5E6(Tc),
  B) pGPTV-D6D5E6(Tc)ω3Pi,
  C) pGPTV-D6D5E6(Tp)ω3Pi
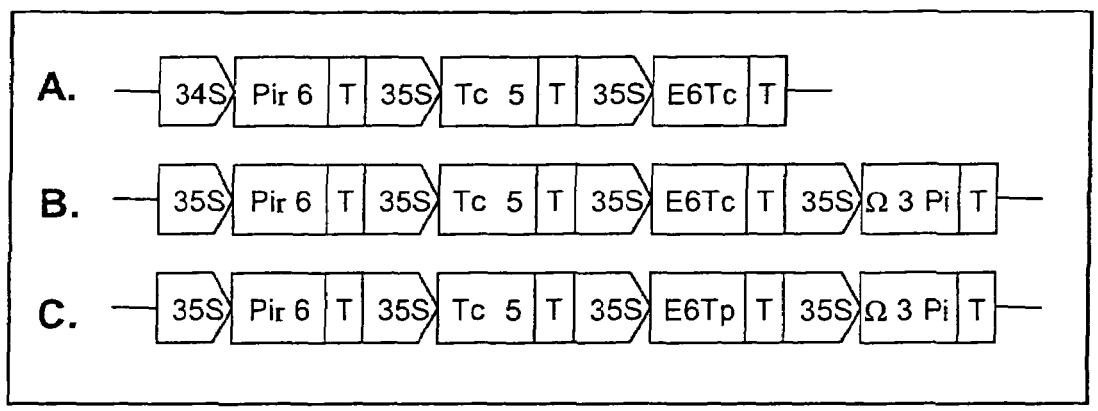

US 8,134,046 B2

METHOD FOR PRODUCING ARACHIDONIC ACID AND/OR EICOSAPENTAENOIC ACID IN USEFUL TRANSGENIC PLANTS

RELATED APPLICATIONS

This application is a national stage application (under 35 U.S.C. §371) of PCT/EP2006/064922 filed Aug. 1, 2006, which claims benefit of German application 10 2005 038 036.0 filed Aug. 9, 2005.

The present invention relates to a process for producing arachidonic acid and/or eicosapentaenoic acid in transgenic useful plants by introducing into the plant nucleic acids coding for polypeptides having Δ6-desaturase, Δ6-elongase or Δ5-desaturase activity. Furthermore, a gene coding for an ω3-desaturase is advantageously expressed in said useful plants. In another advantageous embodiment of the process, further nucleic acid sequences coding for polypeptides of fatty acid or lipid metabolism biosynthesis may be expressed in the plants. Particularly advantageous nucleic acid sequences here are those coding for a Δ8-desaturase, Δ12-desaturase, Δ15-desaturase, Δ4-desaturase, Δ9-elongase and/or Δ5-elongase activity.

The invention further relates to the use of the oils, lipids and/or fatty acids produced in the process according to the invention in feedstuffs or foodstuffs, cosmetics or pharmaceuticals.

Fatty acids and triacylglycerides have a multiplicity of applications in the food industry, in animal nutrition, in cosmetics and in the pharmaceutical sector. They are suitable for a wide variety of applications, depending on whether they are free saturated and unsaturated fatty acids or triacylglycerides having an increased amount of saturated or unsaturated fatty acids. Polyunsaturated ω3 fatty acids and ω6 fatty acids are important constituents of animal feed and human food.

Polyunsaturated long-chain ω3 fatty acids such as eicosapentaenoic acid (=EPA, $C20:5^{\Delta5,8,11,14,17}$) or docosahexaenoic acid (=DHA, $C22:6^{\Delta4,7,10,13,16,19}$) are important components in human nutrition owing to their various roles in health, which comprise aspects such as the development of the child's brain, the functionality of the eye, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids.

Owing to the currently customary composition of human food, an addition of polyunsaturated ω3 fatty acids, which are preferentially found in fish oils, to the food is particularly important. Thus, for example, polyunsaturated fatty acids such as docosahexaenoic acid (=DHA, $C22:6^{\Delta4,7,10,13,16,19}$) or eicosapentaenoic acid (=EPA, $C20:5^{\Delta5,8,11,14,17}$) are added to infant formula to improve the nutritional value.

Hereinbelow, polyunsaturated fatty acids are referred to as PUFA, PUFAs, LCPUFA or LCPUFAs (poly unsaturated fatty acids, PUFA; long chain poly unsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as EPA, dihomo-γ-linolenic acid ($C20:3^{\Delta8,11,14}$) or arachidonic acid (=ARA, $C20:4^{\Delta5,8,11,14}$) are not synthesized in oil crops such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω3 fatty acids are said to have a positive effect on the cholesterol level in the blood and thus on the possibility of preventing heart disease. The risk of heart disease, stroke or hypertension can be reduced markedly by adding these ω3 fatty acids to the food. Also, ω3 fatty acids can have a positive effect on inflammatory, specifically on chronically inflammatory, processes in association with immunological diseases such as rheumatoid arthritis. They are therefore added to foodstuffs, specifically to dietetic foodstuffs, or are employed in medicaments.

ω3 and ω6 fatty acids are precursors of tissue hormones, known as eicosanoids, such as the prostaglandins, which are derived from dihomo-γ-linolenic acid, arachidonic acid and eicosapentaenoic acid, the thromboxanes and leukotrienes, which are derived from arachidonic acid and eicosapentaenoic acid. Eicosanoids (known as the $PG_2$ series) which are formed from ω6 fatty acids generally promote inflammatory reactions, while eicosanoids (known as the $PG_3$ series) from ω3 fatty acids have little or no proinflammatory effect.

Owing to the positive characteristics of the polyunsaturated fatty acids, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347,1990: 200-203 or Huang et al., Lipids 34, 1999: 649-659. As a rule, membrane-bound desaturases are characterized by being introduced into a suitable organism which is subsequently analyzed for enzyme activity by analyzing the starting materials and the products. Δ6-desaturases are described in WO 93/06712, U.S. Pat. No. 5,614,393, WO 96/21022, WO 00/21557 and WO 99/27111 and the application for the production in transgenic organisms is described in WO 98/46763, WO 98/46764 and WO 98/46765. In this context, the expression of various desaturases and the formation of polyunsaturated fatty acids is also described and claimed in WO 99/64616 or WO 98/46776.

The polyunsaturated fatty acids may be divided according to their desaturation patterns into two large classes, ω6 or ω3 fatty acids, which have metabolically and functionally different activities. The synthesis of the ω6 or ω3 fatty acids, arachidonic acid and EPA, via various biosynthetic pathways in microorganisms such as yeasts are described, for example, in WO0159128, WO0012720, WO02077213 and WO0208401.

The fatty acid linoleic acid ($18:2^{\Delta9,12}$) acts as the starting product for the ω6 metabolic pathway, while the ω3 pathway proceeds via linolenic acid ($18:3^{\Delta9,12,15}$). Linolenic acid is produced here due to the activity of an ω3-desaturase (Tocher et al. 1998, Prog. Lipid Res. 37, 73-117; Domergue et al. 2002, Eur. J. Biochem. 269, 4105-4113).

Mammals and therefore also humans do not possess any corresponding desaturase activity (Δ12- and ω3-desaturase)

and must take up these fatty acids (essential fatty acids) via the food. From these precursors, the physiologically important polyunsaturated fatty acids arachidonic acid (=ARA, $20:4^{\Delta 5,8,11,14,17}$), an ω6 fatty acid, and the ω3 fatty acid eicosapentaenoic acid (=EPA, $20:5^{\Delta 5,8,11,14,17}$) are then synthesized via the sequence of desaturase and elongase reactions. In this connection, the administration of ω3 fatty acids exhibits the therapeutic effect as described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

The processes for producing arachidonic acid and/or eicosapentaenoic acid known to date have some disadvantages. Said processes usually produce a mixture of both fatty acids. The only known process for producing arachidonic acid with low proportions of EPA is a fungal, fermentative process. This is an oil source which is suboptimal with regard to nutrition physiology, since it comprises fatty acids which do not occur anywhere else in human food. Another possible source of arachidonic acid is egg lipids. These, however, comprise high proportions of phospholipids and also cholesterol, both of which are rather disadvantageous for widespread use in foodstuffs.

Higher plants comprise polyunsaturated fatty acids such as linoleic acid (C18:2) and linolenic acid (C18:3). ARA and/or EPA are found in the seed oil of higher plants only in traces, if at all (E. Ucciani: Nouveau Dictionnaire des Huiles Végétales. Technique & Documentation—Lavoisier, 1995. ISBN: 2-7430-0009-0). However, production of LCPUFAs in higher plants, preferably in oil crops such as oilseed rape, linseed, sunflower and soybeans, would be advantageous, since it is possible to obtain in this way large amounts of high quality LCPUFAs for the food industry, animal nutrition and for pharmaceutical purposes in a cost-effective manner.

By way of example, DE 102 19 203 (Verfahren zur Herstellung mehrfach ungesättigter Fettsäuren in Pflanzen [Process for producing polyunsaturated fatty acids in plants]) has described for the first time first transgenic plants that harbor and express genes coding for LCPUFA biosynthesis enzymes and produce LCPUFAs. However, these plants produce LCPUFAs in amounts which require further optimization for processing the oils present in said plants.

In order to enrich food and/or animal feed with these polyunsaturated fatty acids, there is therefore still a great need for a simple, inexpensive process for producing arachidonic acid and/or eicosapentaenoic acid.

BRIEF SUMMARY OF THE INVENTION

It was therefore the object to develop a simple, inexpensive, economical process for producing arachidonic acid and/or eicosapentaenoic acid, which does not have the abovementioned disadvantages. Moreover, such a process should enable virtually any amounts of said fatty acids to be synthesized in a cost-effective manner. Apart from the valuable products, arachidonic acid and/or eicosapentaenoic acid, advantageously as few other PUFAs as possible should comprise only either ω3 or ω6 fatty acids, advantageously only ω3 fatty acids.

This object was achieved by the process according to the invention for producing arachidonic acid or eicosapentaenoic acid or arachidonic acid and eicosapentaenoic acid in transgenic useful plants with a content of at least 4% by weight based on the total lipid content of the transgenic useful plant, wherein said process comprises the following steps:

a) introducing at least one nucleic acid sequence coding for a Δ6-desaturase into said useful plant, and
b) introducing at least one nucleic acid sequence coding for a Δ6-elongase into said useful plant, and
c) introducing at least one nucleic acid sequence coding for a Δ5-desaturase into said useful plant, and wherein the sequences indicated in steps (a) to (c) are expressed with the aid of at least one constitutive promoter and terminator in the plants.

Advantageously, the abovementioned nucleic acid sequences used in the process according to the invention and coding for polypeptides having Δ6-desaturase, Δ6-elongase or Δ5-desaturase activity are selected from the group consisting of:

a) a nucleic acid sequence having the sequence depicted in SEQ ID NO: 1, SEQ ID NO: 3, SEQ ID NO: 5 or SEQ ID NO: 7, or
b) nucleic acid sequences which can be derived from the amino acid sequences depicted in SEQ ID NO: 2, SEQ ID NO: 4, SEQ ID NO: 6 or SEQ ID NO: 8 due to the degeneracy of the genetic code, or
c) derivatives of the nucleic acid sequence depicted in SEQ ID NO: 1, SEQ ID NO: 3, SEQ ID NO: 5 or SEQ ID NO: 7 which code for polypeptides that are at least 40% homologous at the amino acid level to SEQ ID NO: 2, SEQ ID NO: 4, SEQ ID NO: 6 or SEQ ID NO: 8 and have a Δ6-desaturase, Δ6-elongase, or Δ5-desaturase activity.

In a preferred embodiment of the process, a nucleic acid sequence coding for an ω3-desaturase is additionally introduced into the useful plants. Said ω3-desaturase-encoding nucleic acid sequence is advantageously selected from the group consisting of:

a) a nucleic acid sequence having the sequence depicted in SEQ ID NO: 9, or
b) nucleic acid sequences which can be derived from the amino acid sequences depicted in SEQ ID NO: 10 due to the degeneracy of the genetic code, or
c) derivatives of the nucleic acid sequence depicted in SEQ ID NO: 9 which code for polypeptides that are at least 40% homologous at the amino acid level to SEQ ID NO: 10 and have an ω3-desaturase activity.

BRIEF DESCRIPTION OF THE DRAWINGS

FIG. 1 gives an overview of the constructs used for plant transformation.

DETAILED DESCRIPTION

Advantageously, the polyunsaturated fatty acids produced in the process according to the invention, ARA and/or EPA, comprise further LCPUFAS of the ω3 or ω6 fatty acid series with at least two, advantageously three, four or five, double bonds. Fatty acids produced in the process advantageously have 18 or 20 carbon atoms in the fatty acid chain, and preferably comprise 20 carbon atoms in the fatty acid chain. Advantageously, saturated fatty acids are converted using the nucleic acids which are used in the process and which code for Δ6-desaturases, Δ6-elongases or Δ5-desaturases and/or ω3-desaturases to a small extent or not at all, advantageously not at all. To a small extent means that, compared to polyunsaturated fatty acids, the saturated fatty acids are converted with less than 5% of the activity, advantageously less than 3%, particularly advantageously with less than 2%, very particularly preferably with less than 1; 0.5; 0.25 or 0.125%. Besides the fatty acids produced in the process, ARA and/or EPA, these may be additionally produced in said process as individual fatty acids or may be present in a fatty acid mixture.

Advantageously, the abovementioned nucleic acid sequences coding for Δ6-desaturases, Δ6-elongases or Δ5-desaturases and/or ω3-desaturases are expressed in combination with other genes of the fatty acid and/or lipid metabolism, such as for example nucleic acid sequences coding for polypeptides having Δ12-desaturase, Δ9-elongase, Δ8-desaturase, Δ5-elongase and/or Δ4-desaturase activity.

The nucleic acids used in the process according to the invention are advantageously expressed in vegetative tissue (=somatic tissue). Vegetative tissue means for the purposes of the present invention that the tissue is characterized by propagating by mitotic divisions. This kind of tissue is also produced by asexual reproduction (=apomixis) and propagation. The term propagation is used if the number of individuals increases in successive generations. These individuals produced by asexual propagation are essentially identical to their parents. Examples of such tissues are leaf, flower, root, stem, runners above or below ground (side shoots, stolons), rhizomes, buds, tubers such as root tubers or stem tubers, bulb, brood bodies, brood buds, bulbils or turions. Such tissues may also be produced by pseudovivipary, true vivipary or vivipary caused by humans. But the vegetative tissues in which expression takes place advantageously also include seeds produced by agamospermy, as is typical for Asteraceae, Poaceae or Rosaceae. The nucleic acids used in the process according to the invention are expressed to a small degree, if at all, in generative tissue (germ line tissue). Examples of such tissues are tissues arising from sexual reproduction, i.e. meiotic cell divisions, such as, for example, seeds produced due to sexual processes. To a small degree means that expression, measured at the RNA and/or protein level, is less than 5%, advantageously less than 3%, particularly advantageously less than 2%, very particularly preferably less than 1; 0.5; 0.25 or 0.125%, compared to vegetative tissue. Generative tissue means for the purposes of the present invention that the tissue is formed due to meiotic division.

The polyunsaturated fatty acids produced in the process are advantageously bound in phospholipids and/or triacylglycerides but may also occur in the organisms as free fatty acids or else bound in the form of other fatty esters. They may be present as "pure products" or else advantageously in the form of mixtures of various fatty acids or mixtures of different phospholipids such as phosphatidyl glycol, phosphatidylcholine, phosphatidylethanolamine and/or phosphatidylserine and/or triacylglycerides, monoacylglycerides and/or diacylglycerides. The LCPUFAS produced in the process, ARA and/or EPA, are advantageously present in phosphatidylcholine and/or phosphatidylethanolamine and/or in the triacylglycerides. Said triacylglycerides may moreover comprise still other fatty acids such as short-chain fatty acids having from 4 to 6 carbon atoms, medium-chain fatty acids having from 8 to 12 carbon atoms or long-chain fatty acids having from 14 to 24 carbon atoms, and preferably comprise long-chain fatty acids, with the long-chain fatty acids particularly preferably being LCPUFAs of $C_{18}$ or $C_{20}$ fatty acids.

The process according to the invention produces advantageously fatty esters with polyunsaturated $C_{18}$ and/or $C_{20}$ fatty acid molecules, with at least two double bonds in the fatty ester, advantageously with at least three, four or five double bonds in the fatty ester, particularly advantageously with four or five double bonds in the fatty ester, advantageously resulting in the synthesis of linoleic acid (=LA, $C18:2^{\Delta9,12}$), γ-linolenic acid (=GLA, $C18:3^{\Delta6,9,12}$), stearidonic acid (=SDA, $C18:4\Delta6,9,12,15$), dihomo-γ-linolenic acid (=DGLA, $20:3^{\Delta8,11,14}$), arachidonic acid (ARA, $C20:4^{\Delta5,8,11,14}$) or eicosapentaenoic acid (EPA, $C20:5^{\Delta5,8,11,14,17}$) or mixtures thereof, preferably ARA and/or EPA. Very particular preference is given to producing the ω3 fatty acid EPA.

The fatty esters with polyunsaturated $C_{18}$ and/or $C_{20}$ fatty acid molecules may be isolated from the useful plants used for producing said fatty esters in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides, or other fatty esters such as the acetyl-coenzyme A esters comprising the polyunsaturated fatty acids with at least two, three or four, preferably three or four, double bonds, and are advantageously isolated in the form of their diacylglycerides, triacylglycerides and/or in the phosphatidyl ester form, particularly preferably in the form of the triacylglycerides, phosphatidylcholine and/or phosphatidylserine. Apart from these esters, the plants comprise the polyunsaturated fatty acids also as free fatty acids or bound in other compounds. The various abovementioned compounds (fatty esters and free fatty acids) are usually present in the organisms in an approximate distribution of from 80 to 90% (w/w) triglycerides, 2 to 5% (w/w) diglycerides, 5 to 10% (w/w) monoglycerides, 1 to 5% (w/w) free fatty acids, 2 to 8% (w/w) phospholipids, with the sum of the various compounds being 100% (w/w).

The LCPUFAs produced in the process according to the invention are produced with a content of at least 4% by weight, advantageously of at least 5, 6, 7, 8, 9 or 10% by weight, preferably of at least 11, 12, 13, 14 or 15% by weight, particularly preferably of at least 16, 17, 18, 19, or 20% by weight, very particularly preferably of at least 25, 30, 35 or 40% by weight, based on total fatty acids in the transgenic plant. In this context, the triacylglycerides and/or phosphatidylglycerides, advantageously phosphatidylcholine and/or phosphatidylserine, comprise the fatty acids produced in the process according to the invention, ARA and/or EPA, with a content of at least 10% by weight, preferably of at least 11, 12, 13, 14 or 15% by weight, particularly preferably of at least 16, 17, 18, 19, or 20% by weight, very particularly preferably of at least 25, 26, 27, 28, 29, 30 or 31% by weight, most preferably of at least 32, 33, 34, 35, 36, 37, 38, 39, 40, 41, 42, 43, 44 or 45% by weight, based on total fatty acids.

The fatty acids are advantageously produced in bound form. It is possible, with the aid of the nucleic acids used in the process according to the invention, to attach these unsaturated fatty acids to the sn1, sn2 and/or sn3 position of the advantageously produced triglycerides. Advantageously, at least 11% of the triacylglycerides are double-substituted, i.e. substituted in the sn1 and sn2 or sn2 and sn3 position. Triple-substituted triacylglycerides are also detectable. Since the starting compounds in the process according to the invention, linoleic acid (C18:2) and linolenic acid (C18:3), respectively, are subjected to a variety of reaction steps, the final products of the process, such as for example arachidonic acid (ARA) or eicosapentaenoic acid (EPA) are not obtained as absolute pure products, but the final product always also comprises traces or larger amounts of the precursors. For example, if the starting plant contains both linoleic acid and linolenic acid, the final products such as ARA or EPA will be present as mixtures. The precursors should advantageously constitute no more than 20% by weight, preferably no more than 15% by weight, particularly preferably no more than 10% by weight, very particularly preferably no more than 5% by weight, based on the amount of the particular final product. Advantageously, a transgenic plant produces as final products only ARA or EPA, either bound or as free acids, in the process according to the invention.

Fatty esters or fatty acid mixtures produced by the process according to the invention advantageously comprise from 6 to 15% palmitic acid, from 1 to 6% stearic acid; 7-85% oleic acid; from 0.5 to 8% vaccenic acid, from 0.1 to 1% arachic acid, from 7 to 25% saturated fatty acids, from 8 to 85% monounsaturated fatty acids, and from 60 to 85% polyunsaturated fatty acids, in each case based on 100% and the total fatty acid content of the organisms. The advantageous polyunsaturated fatty acid present in the fatty esters or fatty acid mixtures is preferably at least 0.1; 0.2; 0.3; 0.4; 0.5; 0.6; 0.7; 0.8; 0.9 or 1% arachidonic acid, based on the total fatty acid content. Furthermore, the fatty esters or fatty acid mixtures produced by the process according to the invention advantageously comprise fatty acids selected from the group of the following fatty acids: erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). Usually, the abovementioned fatty acids are advantageously found only in traces in the fatty esters or fatty acid mixtures produced by the process according to the invention, i.e. they constitute less than 30%, preferably less than 25%, 24%, 23%, 22% or 21%, particularly preferably less than 20%, 15%, 10%, 9%, 8%, 7%, 6% or 5%, very particularly preferably less than 4%, 3%, 2% or 1%, based on total fatty acids. In a further preferred form of the invention, said abovementioned fatty acids constitute less than 0.9%; 0.8%; 0.7%; 0.6%; or 0.5%, particularly preferably less than 0.4%; 0.3%; 0.2%; 0.1%, based on total fatty acids. The fatty esters or fatty acid mixtures produced by the process according to the invention advantageously comprise less than 0.1%, based on total fatty acids, and/or no butyric acid, no cholesterol, no clupanodonic acid (=docosapentaenoic acid, $C22:5^{\Delta 4,8,12,15,21}$) and also no nisinic acid (tetracosahexaenoic acid, $C23:6^{\Delta 3,8,12,15,18,21}$).

The nucleic acid sequences used in the process according to the invention can increase the yield of polyunsaturated fatty acids by at least 50%, advantageously by at least 80%, particularly advantageously by at least 100%, very particularly advantageously by at least 150%, over the nontransgenic useful plants, see examples.

Chemically pure polyunsaturated fatty acids or fatty acid compositions can also be synthesized by the processes described above. For this purpose, the fatty acids or fatty acid compositions are isolated from the plants in a known manner, for example by extraction, distillation, crystallization, chromatography or combinations of these methods. These chemically pure fatty acids or fatty acid compositions are advantageous for applications in the food, the cosmetic and particularly the pharmaceutical industry sectors.

In principle, all dicotyledonous or monocotyledonous useful plants are suitable for the process according to the invention. Useful plants mean plants which are used for food production for humans and animals, the production of luxury consumable items, fibers and pharmaceuticals, such as cereals, for example corn, rice, wheat, barley, millet, oats, rye, buckwheat; such as tubers, for example potato, manioc, batate, yams etc.; such as sugar plants, for example, sugar cane or sugar beet; such as legumes, for example beans, peas, field bean etc.; such as oil and fat plants, for example soybean, oilseed rape, sunflower, safflower, linseed, camelina etc., to name but a few. Advantageous plants are selected from the group of plant families consisting of the following families: Aceraceae, Actinidiaceae, Anacardiaceae, Apiaceae, Arecaceae, Asteraceae, Arecaceae, Betulaceae, Boraginaceae, Brassicaceae, Bromeliaceae, Cannabaceae, Cannaceae, Caprifoliaceae, Chenopodiaceae, Convolvulaceae, Cucurbitaceae, Dioscoreaceae, Elaeagnaceae, Ericaceae, Euphorbiaceae, Fabaceae, Fagaceae, Grossulariaceae, Juglandaceae, Lauraceae, Liliaceae, Linaceae, Malvaceae, Moraceae, Musaceae, Oleaceae, Oxalidaceae, Papaveraceae, Poaceae, Polygonaceae, Punicaceae, Rosaceae, Rubiaceae, Rutaceae, Scrophulariaceae, Solanaceae, Sterculiaceae and Valerianaceae.

Examples which may be mentioned are the following plants selected from the group consisting of: Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus*[chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [African or French marigold], Apiaceae such as the genus *Daucus*, for example the genus and species *Daucus carota* [carrot], Betulaceae such as the genus *Corylus*, for example the genera and species *Corylus avellana* or *Corylus colurna* [hazelnut], Boraginaceae such as the genus *Borago*, for example the genus and species *Borago officinalis* [borage], Brassicaceae such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabidopsis thaliana*, Bromeliaceae such as the genera *Anana, Bromelia* (*Ananas*), for example the genera and species *Anana comosus, Ananas ananas* or *Bromelia comosa* [pineapple], Caricaceae such as the genus *Carica* such as the genus and species *Carica papaya* [papaya], Cannabaceae such as the genus *Cannabis* such as the genus and species *Cannabis sative* [hemp], Convolvulaceae such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae such as the genus *Beta* such as the genera and species *Beta vulgaris, Beta vulgaris* var. *altissima, Beta vulgaris* var. *vulgaris, Beta maritima, Beta vulgaris* var. *perennis, Beta vulgaris* var. *conditiva* or *Beta vulgaris* var. *esculenta* [sugar beet], Cucurbitaceae such as the genus *Cucurbita*, for example the genera and species *Cucurbita maxima, Cucurbita mixta, Cucurbita pepo* or *Cucurbita moschata* [pumpkin/squash], Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus*, soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa] *Glycine max Dolichos soja, Glycine gracilis, Glycine hispida, Phaseolus max, Soja hispida* or *Soja max* [soybean], Geraniaceae such as the genera *Pelargonium, Cocos, Oleum*, for example the genera and species *Cocos nucifera, Pelargonium grossularioides* or *Oleum cocois* [coconut], Gramineae such as the genus *Saccharum*, for example the genus and species *Saccharum officinarum*, Juglandaceae such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae such as the genera *Persea, Laurus*, for example the genera and species *Laurus nobilis* [bay], *Persea americana, Persea gratissima* or *Persea persea* [avocado], Leguminosae such as the genus *Arachis*, for example the genus and species *Arachis hypogaea* [peanut], Linaceae such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae such as the genus *Punica*, for example the genus and species *Punica granatum* [pomegranate], Malvaceae such as the genus *Gossypium*, for example the genera and species *Gossypium hirsutum, Gossypium arboreum, Gossypium barbadense, Gossypium herbaceum* or *Gossypium thurberi* [cotton], Musaceae such as the genus *Musa*, for example the genera and species *Musa nana, Musa acuminata, Musa paradisiaca, Musa* spp. [banana], Onagraceae such as the genera *Camissonia, Oenothera*, for example the genera and species *Oenothera biennis* or *Camissonia brevipes* [evening primrose], Palmae such as the genus *Elacis*, for example the genus and species *Elaeis guineensis* [oil palm], Papaveraceae such as the genus *Papaver*, for example the genera and species *Papaver orientale, Papaver rhoeas, Papaver dubium* [poppy], Pedaliaceae such as the genus *Sesamum*, for example the genus and species *Sesamum indicum* [sesame], Piperaceae such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae such as the genera *Hordeum, Secale, Avena, Sorghum, Andropogon, Holcus, Panicum, Oryza, Zea* (corn), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cemuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [corn]*Triticum aestivum, Triticum durum, Triticum turgidum, Triticum hybernum, Triticum macha, Triticum sativum* or *Triticum vulgare* [Wheat], Porphyridiaceae such as the genera *Chroothece, Flintiella, Petrovanella, Porphyridium, Rhodella, Rhodosorus, Vanhoeffenia*, for example the genus and species *Porphyridium cruentum*, Proteaceae such as the genus *Macadamia*, for example the genus and species *Macadamia intergrifolia* [macadamia], Rubiaceae such as the genus *Coffea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [verbascum], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant] *Lycopersicon esculentum, Lycopersicon lycopersicum, Lycopersicon pyriforme, Solanum integrifolium* or *Solanum lycopersicum* [tomato], Sterculiaceae such as the genus *Theobroma*, for example the genus and species *Theobroma cacao* [cocoa] or Theaceae such as the genus *Camellia*, for example the genus and species *Camellia sinensis* [tea].

In an advantageous embodiment of the process, the useful plants used are oil plants which comprise large amounts of lipid compounds, such as peanut, oilseed rape, canola, sunflower, safflower (*Carthamus tinctoria*), poppy, mustard, hemp, castor-oil plant, olive, sesame, calendula, Punica, evening primrose, verbascum, thistle, wild roses, hazelnut, almond, macadamia, avocado, bay, pumpkin, linseed, soybean, pistachios, borage, trees (oil palm, coconut or walnut) or crops such as corn, wheat, rye, oats, triticale, rice, barley, cotton, manioc, pepper, marigold, Solanaceae such as potato, tobacco, eggplant and tomato, *Vicia* species, pea, alfalfa or shrubs (coffee, cocoa, tea), *Salix* species and hardy grasses and feedcrops. Advantageous plants according to the invention are oil plants such as peanut, oilseed rape, canola, sunflower, safflower, poppy, mustard, hemp, castor-oil plant, olive, calendula, Punica, evening primrose, pumpkin/squash, linseed, soybean, borage, trees (oil palm, coconut). Particular preference is given to C18:2 and/or C18:3 fatty acid-rich plants such as sunflower, safflower, tobacco, verbascum, sesame, cotton, pumpkin/squash, poppy, evening primrose, walnut, linseed, hemp, thistle or safflower. Very particular preference is given to plants such as safflower, sunflower, poppy, evening primrose, walnut, linseed or hemp.

It is advantageous for the described process according to the invention to introduce into the plants additionally further nucleic acids which code for enzymes of the fatty acid or lipid metabolism, in addition to the nucleic acids introduced in process steps (a) to (c) and the optionally introduced nucleic acid sequences coding for the ω3-desaturases.

In principle it is possible to use any genes of the fatty acid or lipid metabolism advantageously in combination with the nucleic acid sequences used in the process according to the invention, which code for Δ6-elongase(s), Δ6-desaturase(s), Δ5-desaturase(s) and/or ω3-desaturase(s) [for the purposes of the present application, the plural is meant to include the singular and vice versa]; genes of the fatty acid or lipid metabolism selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s) are advantageously used in combination with said Δ6-elongase, Δ6-desaturase, Δ5-desaturase and/or ω3-desaturase. Particular preference is given to using genes selected from the group consisting of Δ4-desaturases, Δ8-desaturases, Δ9-desaturases, Δ12-desaturases, Δ5-elongases or Δ9-elongases in combination with the abovementioned genes for said Δ6-elongase, Δ6-desaturase, Δ5-desaturase and/or ω3-desaturase, it being possible to use individual genes or a plurality of genes in combination.

The ω3-desaturase used in the process according to the invention should advantageously make possible a shift from the ω6-biosynthetic pathway to the ω3-biosynthetic pathway, resulting advantageously in a shift from $C_{18:2}$- to $C_{18:3}$ fatty acids. These properties of ω3-desaturase advantageously enable the fatty acid spectrum in an organism, advantageously in a plant or a fungus, to be shifted from the ω6 fatty acids to the ω3 fatty acids. It is furthermore advantageous that said ω3-desaturase converts a wide range of phospholipids such as phosphatidylcholine (=PC), phosphatidylinositol (=PIS) or phosphatidylethanolamine (=PE). Finally, desaturation products can also be found in the neutral lipids (=NL), i.e. in the triglycerides.

Owing to the enzymatic activity of the nucleic acids used in the process according to the invention, which code for polypeptides having Δ6-elongase, Δ6-desaturase, Δ5-desaturase and/or ω3-desaturase activity, advantageously in combination with nucleic acid sequences coding for polypeptides of the fatty acid or lipid metabolism such as further polypeptides having Δ4-, Δ-5-, Δ-6-, Δ8-, Δ12-desaturase or Δ5-, Δ-6- or Δ9-elongase activity, a wide variety of polyunsaturated fatty acids can be produced in the process according to the invention. Depending on the choice of the useful plants used for the process according to the invention, mixtures of the various polyunsaturated fatty acids or individual polyunsaturated fatty acids such as EPA or ARA can be produced in free or bound form. Depending on the dominant fatty acid composition in the starting plant (C18:2- or C18:3 fatty acids), fatty acids are thus produced which derive from C18:2 fatty acids, such as GLA, DGLA or ARA, or which derive from C18:3 fatty acids, such as SDA, ETA or EPA. If the only unsaturated fatty acid present in the plant used for the process is linoleic acid (=LA, $C18:2^{\Delta9,12}$), said process can produce only GLA, DGLA and ARA which may be in the form of free fatty acids or in bound form. If the only unsaturated fatty acid in the plant used in the process is α-linolenic acid (=ALA, $C18:3^{\Delta9,12,15}$), as is the case in linseed, for example, said process can produce only SDA, ETA and/or EPA, all of which may be present in the form of fatty acids or in bound form, as described above. By modifying the activity of the enzymes used in the process and involved in the synthesis, Δ6-elongase, Δ6-desaturase, Δ5-desaturase and/or ω3-desaturase, advantageously in combination with further genes of the lipid or fatty acid metabolism, it is possible to specifically produce only individual products in the plants. Advantageously, only ARA or EPA or mixtures thereof are synthesized, depending on the fatty acid present in the organism or in the plant, which is used as starting substance for the synthesis. Since said synthesis involves biosynthetic chains, the respective final products present in the organisms are not pure substances. Small amounts of the precursor compounds are always also present in the final product. These small amounts amount to less than 20% by weight, advantageously less than 15% by weight, particularly advantageously less than 10% by weight, very particularly advantageously less than 5, 4, 3, 2 or 1% by weight, based on the EPA or ARA final product or their mixtures.

Aside from producing the starting fatty acids for the process according to the invention directly inside the plant, the fatty acids may in principle also be fed from the outside. Production inside the plant is preferred for economic reasons. Preferred substrates of ω3-desaturase are linoleic acid ($C18:2^{\Delta9,12}$), γ-linolenic acid ($C18:3^{\Delta6,9,12}$), eicosadienoic acid ($C20:2^{\Delta11,14}$), dihomo-γ-linolenic acid ($C20:3^{\Delta8,11,14}$) and arachidonic acid ($C20:4^{\Delta5,8,11,14}$).

To increase the yield in the above-described process for producing oils and/or triglycerides with an advantageously increased content of polyunsaturated fatty acids, it is advantageous to increase the amount of starting product for fatty acid synthesis, and this may be achieved, for example, by introducing into the organism a nucleic acid which codes for a polypeptide with Δ12-desaturase. This is particularly advantageous in useful plants that comprise oleic acid, such as oil-producing plants such as plants of the Brassicaceae family, such as the genus *Brassica*, for example oilseed rape; the Elaeagnaceae family, such as the genus *Elaeagnus*, for example the genus and species *Olea europaea* or the Fabaceae family, such as the genus *Glycine*, for example the genus and species *Glycine max*, which are high in oleic acid. Since these organisms are only low in linoleic acid (Mikoklajczak et al., Journal of the American Oil Chemical Society, 38, 1961, 678-681), using the abovementioned Δ12-desaturases for producing the starting product, linoleic acid, is advantageous.

Nucleic acids used in the process according to the invention are advantageously derived from plants such as algae, for example algae of the Prasinophyceae family, such as those of the genera *Heteromastix, Mammella, Mantoniella, Micromonas, Nephroselmis, Ostreococcus, Prasinocladus, Prasinococcus, Pseudoscourfielda, Pycnococcus, Pyramimonas, Scherffelia* or *Tetraselmis* such as the genera and species *Heteromastix longifillis, Mamiella gilva, Mantoniella squamata, Micromonas pusilla, Nephroselmis olivacea, Nephroselmis pyriformis, Nephroselmis rotunda, Ostreococcus tauri, Ostreococcus* sp., *Prasinocladus ascus, Prasinocladus lubricus, Pycnococcus provasolii, Pyramimonas amylifera, Pyramimonas disomata, Pyramimonas obovata, Pyramimonas orientalis, Pyramimonas parkeae, Pyramimonas spinifera, Pyramimonas* sp., *Tetraselmis apiculata, Tetraselmis carteriaformis, Tetraselmis chui, Tetraselmis convolutae, Tetraselmis desikacharyl, Tetraselmis gracilis, Tetraselmis hazeni, Tetraselmis impellucida, Tetraselmis inconspicua, Tetraselmis levis, Tetraselmis maculata, Tetraselmis marina, Tetraselmis striata, Tetraselmis subcordiformis, Tetraselmis suecica, Tetraselmis tetrabrachia, Tetraselmis tetrathele, Tetraselmis verrucosa, Tetraselmis verrucosa* fo. rubens or *Tetraselmis* sp. or from algae of the Euglenaceae family, such as those of the genera *Ascoglena, Astasia, Colacium, Cyclidiopsis, Euglena, Euglenopsis, Hyalophacus, Khawkinea, Lepocinclis, Phacus, Strombomonas* or *Trachelomonas* such as the genera and species *Euglena acus, Euglena geniculata, Euglena gracilis, Euglena mixocylindracea, Euglena rostrifera, Euglena viridis, Colacium stentorium, Trachelomonas cylindrica* or *Trachelomonas volvocina*. Advantageously, the nucleic acids used are derived from algae of the genera *Euglena, Mantoniella* or *Ostreococcus*.

Other advantageous plants are algae such as *Isochrysis* or *Crypthecodinium*, algae/diatoms such as *Thalassiosira* or *Phaeodactylum*, mosses such as *Physcomitrella* or *Ceratodon* or higher plants such as the Primulaceae such as *Aleuritia, Calendula stellata, Osteospermum spinescens* or *Osteospermum hyoseroides*, microorganisms such as fungi such as *Aspergillus, Thraustochytrium, Phytophthora, Entomophthora, Mucor* or *Mortierella*, bacteria such as *Shewanella*, yeasts or animals such as nematodes such as *Caenorhabditis*, insects, frogs, sea cucumber or fish. The isolated nucleic acid sequences according to the invention are advantageously derived from an animal of the order of the vertebrates. Preference is given to said nucleic acid sequences deriving from the following classes: Vertebrata; Euteleostomi, Actinopterygii; Neopterygii; Teleostei; Euteleostei, Protacanthopterygii, Salmoniformes; Salmonidae or *Oncorhynchus* or Vertebrata, Amphibia, Anura, Pipidae, *Xenopus* or Evertebrata, such as Protochordata, Tunicata, Holothuroidea, Cionidae, such as *Amaroucium constellatum, Botryllus schlosseri, Ciona intestinalis, Molgula citrina, Molgula manhattensis, Perophora viridis* or *Styela partita*. Particularly advantageously the nucleic acids are derived from fungi, animals or from plants such as algae or mosses, preferably of the Salmoniformes order, such as the Salmonidae family, such as the genus *Salmo*, for example of the genera and species *Oncorhynchus mykiss, Trutta trutta* or *Salmo trutta fario*, from algae such as the genera *Mantoniella* or *Ostreococcus*, or from the diatoms such as the genera *Thalassiosira* or *Phaeodactylum*, or from algae such as *Crypthecodinium*.

The abovementioned nucleic acid sequences or their derivative or homologs which code for polypeptides that retain the enzymic activity of the nucleic acid sequence-encoded proteins become advantageous in the process according to the invention. Said sequences are cloned either individually or in combination with the nucleic acid sequences coding for, $\Delta 12$-desaturase, $\Delta 4$-desaturase, $\Delta 5$-desaturase, $\Delta 6$-desaturase, $\Delta 5$-elongase, $\Delta 6$-elongase and/or $\omega 3$-desaturase into expression constructs and used for the introduction into, and expression in, organisms. Owing to their construction, these expression constructs enable the polyunsaturated fatty acids produced in the process according to the invention to be synthesized in an advantageous and optimal manner.

In a preferred embodiment, the process further comprises the step of obtaining a cell or a whole plant which comprises the nucleic acid sequences used in said process which code for a $\Delta 6$-desaturase, $\Delta 6$-elongase, $\Delta 5$-desaturase and/or $\omega 3$-desaturase, wherein the cell and/or the useful plant may also comprise further nucleic acid sequences of the lipid or fatty acid metabolism. These nucleic acid sequences used preferentially in the process are advantageously incorporated for expression into at least one gene construct and/or a vector, as described below, alone or in combination with further nucleic acid sequences coding for proteins of the fatty acid or lipid metabolism, and finally transformed into the cell or plant. In a further preferred embodiment, said process also comprises the step of obtaining the oils, lipids or free fatty acids from the useful plants. The cell produced in this way or the useful plant produced in this way is advantageously a cell of an oil-producing plant, vegetable plant, salad plant or ornamental, or the plant itself, as explained above.

Cultivation means, for example, in the case of plant cells, plant tissue or plant organs, culturing on or in a nutrient medium, or culturing the whole plant on or in a substrate, for example, in hydroponic culture, potting compost or on arable land.

"Transgenic" or "recombinant" means, for the purposes of the invention and with regard to a nucleic acid sequence, an expression cassette (=gene construct) or a vector comprising the nucleic acid sequences used in the process according to the invention, or to a plant transformed with the nucleic acid sequences, expression cassette or vector used in the process according to the invention, for example, all those constructions brought about by genetic engineering methods, in which either a) the nucleic acid sequence, or
b) a genetic control sequence functionally linked to said nucleic acid sequence, for example a promoter, or
c) (a) and (b)

are not within their natural, genetic environment or have been modified by genetic engineering methods, it being possible for said modification to be, for example, a substitution, addition, deletion, inversion or insertion of one or more nucleotide residues. Natural genetic environment means the natural genomic or chromosomal locus in the source organism or the presence in a genomic library. In the case of a genomic library, the natural, genetic environment of the nucleic acid sequence is preferably at least partially retained. Said environment flanks the nucleic acid sequence at least on one side and has a sequence length of at least 50 bp, preferably at least 500 bp, particularly preferably at least 1000 bp, very particularly preferably at least 5000 bp. A naturally occurring expression cassette—for example the naturally occurring combination of the natural promoter of the nucleic acid sequence used in the process according to the invention, which sequence codes for proteins having a corresponding $\Delta 6$-desaturase, $\Delta 6$-elongase, $\Delta 5$-desaturase and/or $\omega 3$-desaturase activity, advantageously in combination with nucleic acid sequences coding for proteins with $\Delta 12$-desaturase, $\Delta 4$-desaturase, $\Delta 8$-desaturase, $\Delta 9$-elongase and/or $\Delta 5$-elongase activity, becomes a transgenic expression cassette when it is altered by nonnatural, synthetic ("artificial") processes such as, for example, mutagenization. Suitable processes are described, for example, in U.S. Pat. No. 5,565,350 or WO 00/15815.

A transgenic plant means for the purposes of the invention, as mentioned above, that the nucleic acids used in the process are not at their natural site in the genome of said plant, it being possible for said nucleic acids to be expressed homologously or heterologously. However, as mentioned above, transgenic also means that the nucleic acids according to the invention are at their natural location in the genome of the plant, that however the sequence has been modified with regard to the natural sequence, and/or that the regulatory sequences of the natural sequences have been modified. Transgenic preferably means expression of the nucleic acids used in the process according to the invention at a nonnatural site in the genome, i.e. homologous, or preferably heterologous, expression of the nucleic acids takes place. Preferred transgenic organisms are useful plants such as oil-producing plants, vegetable plants, salad plants or ornamentals, all of which are advantageously selected from the group of plant families, consisting of the following families: Aceraceae, Actinidiaceae, Anacardiaceae, Apiaceae, Arecaceae, Asteraceae, Arecaceae, Betulaceae, Boraginaceae, Brassicaceae, Bromeliaceae, Cannabaceae, Cannaceae, Caprifoliaceae, Chenopodiaceae, Convolvulaceae, Cucurbitaceae, Dioscoreaceae, Elaeagnaceae, Ericaceae, Euphorbiaceae, Fabaceae, Fagaceae, Grossulariaceae, Juglandaceae, Lauraceae, Liliaceae, Linaceae, Malvaceae, Moraceae, Musaceae, Oleaceae, Oxalidaceae, Papaveraceae, Poaceae, Polygonaceae, Punicaceae, Rosaceae, Rubiaceae, Rutaceae, Scrophulariaceae, Solanaceae, Sterculiaceae and Valerianaceae.

Suitable host plants for the nucleic acids, the expression cassette or the vector used in the process according to the invention are in principle and advantageously any useful plants which are capable of synthesizing fatty acids, especially unsaturated fatty acids, or which are suitable for expression of recombinant genes. Examples which may be mentioned here are plants such as *Arabidopsis*, Asteraceae such as *Calendula*, or useful plants such as soybean, peanut, castor-oil plant, sunflower, corn, cotton, flax, oilseed rape, coconut, oil palm, safflower (*Carthamus tinctorius*) or cacao bean. Other advantageous plants are listed elsewhere in the present application.

The transgenic useful plant is usually prepared using microorganisms as intermediate hosts. Such usable intermediate host cells are mentioned in: Goeddel, Gene Expression Technology Methods in Enzymology 185, Academic Press, San Diego, Calif. (1990).

Advantageously usable expression strains for this purpose are, for example, those which have a lower protease activity. They are described, for example, in: Gottesman, S., Gene Expression Technology: Methods in Enzymology 185, Academic Press, San Diego, Calif. (1990) 119-128.

Transgenic plants which comprise the polyunsaturated fatty acids synthesized in the process according to the invention can advantageously be marketed directly, without any need for the synthesized oils, lipids or fatty acids to be isolated. This kind of marketing is particularly advantageous.

Among plants in the process according to the invention are, as described above, whole plants and also any plant parts, plant organs or plant parts such as leaf, stem, seed, root, tubers, anthers, fibers, root hairs, stalks, embryos, kalli, cotyledons, petioles, harvested material, plant tissue, reproductive tissue and cell cultures which are derived from the transgenic plant and/or can be used for generating the transgenic plant. In this context, the seed comprises all seed parts such as the seed coats, epidermal cells, seed cells, endosperm or embryonic tissue. However, the compounds produced in the process according to the invention may also be isolated from the plants in the form of their oils, fat, lipids and/or free fatty acids. Polyunsaturated fatty acids produced by this process can be obtained by harvesting the plants or plant cells, either from the culture in which they grow, or from the field. This may be done via pressing or extracting the plant parts, preferably the plant seeds. In this context, the oils, fats, lipids and/or free fatty acids can be obtained by what is known as cold beating or cold pressing, with no heat being supplied due to pressing. The plant parts, especially the seeds, are comminuted, steamed or roasted beforehand, so that they can be broken more readily. The seeds pretreated in this way can then be pressed or extracted with solvent such as warm hexane. The solvent is subsequently removed. In this way, more than 96% of the compounds produced in the process can be isolated. The products obtained in this way are then processed further, i.e. refined. This involves firstly removing, for example, the plant mucilages and suspended matter. "Desliming" may be effected enzymically or, for example, chemically/physically by adding acid such as phosphoric acid. The free fatty acids are then removed by treatment with a base, for example, sodium hydroxide solution. The resulting product is washed thoroughly with water to remove the alkali remaining in the product and dried. To remove the pigments still remaining in the product, the products are subjected to bleaching, for example using Fuller's earth or activated carbon. Finally, the product is also deodorized, for example using steam.

The PUFAs and LCPUFAs produced by this process are preferably $C_{18}$-, and/or $C_{20}$ fatty acid molecules, advantageously $C_{20}$ fatty acid molecules, with at least two double bonds in the fatty acid molecule, preferably three, four or five double bonds. These $C_{18}$- and/or $C_{20}$ fatty acid molecules can be isolated from the plant in the form of an oil, lipid or a free fatty acid. Examples of suitable transgenic plants are those mentioned above.

One embodiment of the invention is therefore the use of said oils, lipids or fatty acids or fractions thereof, which have been produced by the above-described process, for the production of feedstuffs, foodstuffs, cosmetics or pharmaceuticals.

Said oils, lipids or fatty acids obtained in this way advantageously comprise, as described above, from 6 to 15% palmitic acid, 1 to 6% stearic acid; 7-85% oleic acid; 0.5 to 8% vaccenic acid, 0.1 to 1% arachic acid, 7 to 25% saturated fatty acids, 8 to 85% monounsaturated fatty acids, and 60 to 85% polyunsaturated fatty acids, in each case based on 100% and on the total fatty acid content of the plants. The fatty esters or fatty acid mixtures, such as phosphatidyl fatty esters or triacylglyceride esters, preferably comprise at least 10; 11; 12; 13; 14; 15; 16; 17; 18; 19 or 20% by weight, based on the total fatty acid content, of arachidonic acid and/or at least 20; 21; 22; 23; 24 or 25, advantageously at least 26, 27, 28, 29 or 30, particularly advantageously at least 31, 32, 33, 34, 35, 36; 37; 38; 39 or 40, very particularly advantageously at least 41, 42, 43, 44, 45% by weight or more, based on the total fatty acid content, of eicosapentaenoic acid as advantageous polyunsaturated fatty acid. Moreover, the fatty esters or fatty acid mixtures which have been produced by the process of the invention advantageously comprise fatty acids selected from the group of the fatty acids erucic. acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9- ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty esters or fatty acid mixtures produced by the process according to the invention, that is to say that, based on total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. In a further preferred form of the invention, these abovementioned fatty acids occur, based on total fatty acids, to less than 0.9%; 0.8%; 0.7%; 0.6%; or 0.5%, particularly preferably to less than 0.4%; 0.3%; 0.2%; 0.1%. Advantageously, the fatty esters or fatty acid mixtures produced by the process according to the invention comprise less than 0.1%, based on total fatty acids, and/or no butyric acid, no cholesterol, no clupanodonic acid (=docosapentaenoic acid, $C22:5^{\Delta 4,8,12,15,21}$) and no nisinic acid (tetracosahexaenoic acid, $C23:6^{\Delta 3,8,12,15,18,21}$).

Another embodiment according to the invention is the use of the oils, lipids, the fatty acids and/or the fatty acid composition produced by the process according to the invention in feedstuffs, foodstuffs, cosmetics or pharmaceuticals. The oils, lipids, fatty acids or fatty acid mixtures obtained in the process according to the invention may be used in the manner known to the skilled worker for mixing with other oils, lipids, fatty acids or fatty acid mixtures of animal origin, such as fish oils, for example. These oils, lipids, fatty acids or fatty acid mixtures which are produced in this way and which are composed of vegetable and animal constituents may also be used for the production of feedstuffs, foodstuffs, cosmetics or pharmaceuticals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid or eicosapentaenoic acid. The content of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting plant.

The polyunsaturated fatty acids with advantageously at least two, three, four or five, particularly advantageously with four or five, double bonds, which are produced in the process are advantageously, as described above, fatty esters, for example sphingolipid esters, phosphoglyceride esters, lipid esters, glycolipid esters, phospholipid esters, monoacylglycerol esters, diacylglycerol esters, triacylglycerol esters or other fatty esters, preferably phospholipid esters and/or triacylglycerol esters.

Starting from the polyunsaturated fatty esters with advantageously at least three, four or five double bonds, which esters have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymic cleavage, and isolated via, for example, phase separation and subsequent acidification via, for example, $H_2SO_4$. The fatty acids can also be liberated directly without the above-described processing step.

After their introduction into a plant or plant cell, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains that also accumulate PUFAs in the triacylglycerol fraction are particularly advantageously suitable for the process according to the invention and thus for the modification of the lipid and PUFA production system in a plant such as a useful plant such as an oil plant, for example oilseed rape, canola, linseed, hemp, soybean, sunflowers and borage. They can therefore be used advantageously in the process according to the invention.

Suitable substrates of the nucleic acids used in the process according to the invention, which code for polypeptides having Δ6-desaturase, Δ6-elongase, Δ5-desaturase and/or ω3-desaturase activity, and/or the other nucleic acids used, such as the nucleic acids coding for polypeptides of the fatty acid or lipid metabolism, selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) are advantageously $C_{16}$-, $C_{18}$- or $C_{20}$ fatty acids. Preference is given to converting the fatty acids converted as substrates in the process in the form of their acyl-CoA esters and/or their phospholipid esters.

To produce the long-chain PUFAs according to the invention, the saturated, monounsaturated $C_{16}$ fatty acids and/or polyunsaturated $C_{18}$ fatty acids must, depending on the substrate, first be desaturated and/or elongated by the enzymatic activity of a desaturase and/or elongase or be just desaturated and then elongated by at least two carbon atoms by an elongase. After one elongation cycle, this enzyme activity results either in $C_{18}$ fatty acids starting from $C_{16}$ fatty acids, or in $C_{20}$ fatty acids starting from $C_{18}$ fatty acids, and after two elongation cycles in $C_{20}$ fatty acids starting from $C_{16}$ fatty acids. The activity of the desaturases and elongases used in the process according to the invention preferably results in $C_{18}$- and/or $C_{20}$ fatty acids, advantageously with at least two double bonds in the fatty acid molecule, preferably with three, four or five double bonds, particularly preferably in $C_{20}$ fatty acids with at least four double bonds in the fatty acid molecule. Particularly preferred products of the process according to the invention are dihomo-γ-linolenic acid, arachidonic acid and/or eicosapentaenoic acid. The $C_{18}$ fatty acids with at least two double bonds in the fatty acid may be elongated by the enzymic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of fatty acids, oils, lipids or fats in the plants which are advantageously used is, for example, in general the seed or cell strata of the seed, so that seed-specific expression of the nucleic acids used in the process makes sense. However, it is obvious that the biosynthesis of fatty acids, oils or lipids need not be limited to the seed tissue, but can also take place in a tissue-specific manner in all the other parts of the plant, for example in epidermal cells or in the tubers. Advantageously, the synthesis by the process according to the invention takes place in the vegetative (somatic) tissue.

In principle, the polyunsaturated fatty acids produced by the process according to the invention in the plants used in the process can be increased in two different ways. Advantageously, the pool of free polyunsaturated fatty acids and/or the proportion of the esterified polyunsaturated fatty acids produced via the process can be enlarged. Advantageously, the pool of esterified polyunsaturated fatty acids in the transgenic plants is enlarged by the process according to the invention, advantageously in the form of the phosphatidyl esters and/or triacyl esters.

The fatty acids obtained in the process are also suitable as starting material for the chemical synthesis of further valuable products. They may be used, for example, combined with one another or alone, for the preparation of pharmaceuticals, foodstuffs, animal feed or cosmetics.

Advantageous nucleic acid sequences used in the process, which code for polypeptides having Δ6-desaturase activity, are isolated nucleic acid sequences selected from the group consisting of:
a) a nucleic acid sequence with the sequence depicted in SEQ ID NO: 1,
b) nucleic acid sequences which can be derived from the amino acid sequence depicted in SEQ ID NO: 2 due to the degeneracy of the genetic code, or
c) derivatives of the nucleic acid sequence depicted in SEQ ID NO: 1, which code for polypeptides that are at least 40% homologous to SEQ ID NO: 2 at the amino acid level and have a Δ6-desaturase activity.

Advantageous nucleic acid sequences used in the process, which code for polypeptides having Δ6-elongase activity, are isolated nucleic acid sequences selected from the group consisting of:

a) a nucleic acid sequence with the sequence depicted in SEQ ID NO: 3 or 7,
b) nucleic acid sequences which can be derived from the amino acid sequence depicted in SEQ ID NO: 4 or 8 due to the degeneracy of the genetic code, or
c) derivatives of the nucleic acid sequence depicted in SEQ ID NO: 3 or 7 which code for polypeptides that are at least 40% homologous to SEQ ID NO: 4 or 8 at the amino acid level and have a Δ6-elongase activity.

Advantageous nucleic acid sequences used in the process, which code for polypeptides having Δ5-desaturase activity, are isolated nucleic acid sequences selected from the group consisting of:
a) a nucleic acid sequence with the sequence depicted in SEQ ID NO: 5,
b) nucleic acid sequences which can be derived from the amino acid sequence depicted in SEQ ID NO: 6 due to the degeneracy of the genetic code, or
c) derivatives of the nucleic acid sequence depicted in SEQ ID NO: 5 which code for polypeptides that are at least 40% homologous to SEQ ID NO: 6 at the amino acid level and have a Δ5-desaturase activity.

Advantageously, further nucleic acid sequences coding for polypeptides having ω3-desaturase activity are used in combination with the abovementioned nucleic acids which code for Δ6-desaturases, Δ6-elongases and/or Δ5-desaturases, are isolated nucleic acid sequences selected from the group consisting of:
a) a nucleic acid sequence with the sequence depicted in SEQ ID NO: 9,
b) nucleic acid sequences which can be derived from the amino acid sequence depicted in SEQ ID NO: 10 due to the degeneracy of the genetic code, or
c) derivatives of the nucleic acid sequence depicted in SEQ ID NO: 9, which code for polypeptides that are at least 60% homologous to SEQ ID NO: 10 at the amino acid level and have a ω3-desaturase activity.

Advantageously, the abovementioned nucleic acid sequences are introduced into gene constructs for expression, said nucleic acids being functionally linked to one or more regulatory signals. In addition, the gene construct may comprise further biosynthesis genes of the fatty acid or lipid metabolism, comprises selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s). Advantageously, biosynthesis genes of the fatty acid or lipid metabolism, selected from the group consisting of Δ4-desaturase, Δ8-desaturase, Δ9-desaturase, Δ12-desaturase, Δ5-elongase, Δ9-elongase and/or Δ15-desaturase, are additionally present.

Advantageously, all the nucleic acid sequences used in the process according to the invention derive from a eukaryotic organism such as a plant, a microorganism or an animal. Preference is given to the nucleic acid sequences deriving from the order Salmoniformes, *Xenopus* or *Ciona*, algae such as *Mantoniella, Crypthecodinium, Euglena* or *Ostreococcus*, fungi such as the genus *Phytophtora*, or from diatoms such as the genera *Thalassiosira* or *Phaeodactylum*.

The nucleic acid sequences used in the process which code for proteins having ω3-desaturase, Δ5-desaturase, Δ6-desaturase and/or Δ6-elongase activity, are introduced advantageously alone or preferably in combination into an expression cassette (=nucleic acid construct) which enables said nucleic acids to be expressed in a plant. The nucleic acid construct may comprise more than one nucleic acid sequence of an enzymic activity such as, for example, a Δ12-desaturase, Δ4-desaturase, Δ5-desaturase, Δ8-desaturase, Δ6-desaturase, Δ5-elongase, Δ6-elongase, Δ9-elongase and/or ω3-desaturase.

To introduce the nucleic acids used in the process, the latter are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step. Suitable cloning vectors are generally known to the skilled worker. These include, in particular, vectors which are capable of replication in microbial systems, that is to say mainly vectors which ensure efficient cloning in yeasts or fungi and which make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the *Agrobacterium*-mediated transformation and the T-DNA-delimiting sequences (T-DNA border). These vector systems preferably also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small and easy to manipulate and to replicate both in *E. coli* and in *Agrobacterium*. These binary vectors include vectors from the series pBIB-HYG, pPZP, pBecks, pGreen. In accordance with the invention, Bin19, pBI101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned with vector fragments which have been prepared in a similar manner, using ligase. In this context, a particular nucleic acid construct, or vector or plasmid construct, can have one or else more than one codogenic gene segment. The codogenic gene segments in these constructs are preferably linked operably with regulatory sequences. The regulatory sequences include, in particular, plant sequences such as the above-described promoters and terminator sequences. The constructs can advantageously be stably propagated in microorganisms, in particular in *Escherichia coli* and *Agrobacterium tumefaciens*, under selective conditions and make possible the transfer of heterologous DNA into plants.

The nucleic acids used in the process, the inventive nucleic acids and nucleic acid constructs, can be introduced into microorganisms and thereafter advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, nucleic acid constructs, and/or vectors used in the process can be used for the recombinant modification of a broad spectrum of plants, so that the latter become better and/or more efficient PUFA producers.

Owing to the introduction of a ω3-desaturase, Δ6-desaturase, Δ6-elongase and/or Δ5-desaturase gene into a plant, alone or in combination with other genes, it is not only possible to increase biosynthesis flux towards the end product, but also to increase, or to create de novo the corresponding triacylglycerol and/or phosphatidyl ester composition. Likewise, the number or activity of other genes which are involved in the import of nutrients which are required for the biosynthesis of one or more fatty acids, oils, polar and/or neutral lipids, can be increased, so that the concentration of these precursors, cofactors or intermediates within the cells or within the storage compartment is increased, whereby the ability of the cells to produce PUFAs as described below is enhanced further. By optimizing the activity or increasing the number of one or more ω3-desaturase, Δ6-desaturase, Δ6-elongase and/or Δ5-desaturase genes which are involved in the biosynthesis of these compounds, or by destroying the activity of one or more genes which are involved in the degradation of these compounds, an enhanced yield, production and/or efficiency of production of fatty acid and lipid molecules in organisms, advantageously in plants, is made possible.

The nucleic acid molecules used in the process according to the invention encode proteins or parts of these, where the proteins or the individual protein or parts thereof comprise(s) an amino acid sequence with sufficient homology to an amino acid sequence which is shown in the sequences SEQ ID NO:2, SEQ ID NO:4, SEQ ID NO:6, SEQ ID NO:8 or SEQ ID NO:10, so that the proteins or parts thereof retain a ω3-desaturase, Δ6-desaturase, Δ6-elongase and/or Δ5-desaturase activity. The proteins or parts thereof which is/are encoded by the nucleic acid molecule(s) preferably retain its/their essential enzymatic activity and the ability of participating in the metabolism of compounds required for the synthesis of cell membranes or lipid bodies in organisms, advantageously in plants, or in the transport of molecules across these membranes. Advantageously, the proteins encoded by the nucleic acid molecules have at least approximately 40%, preferably at least approximately 50% or 60% and more preferably at least approximately 70%, 80% or 90% and most preferably at least approximately 85%, 86%, 87%, 88%, 89%, 90%, 91%, 92%, 93%, 94%, 95%, 96%, 97%, 98%, 99% or more identity with the amino acid sequences shown in SEQ ID NO:2, SEQ ID NO:4, SEQ ID NO:6, SEQ ID NO:8 or SEQ ID NO:10. For the purposes of the invention, homology or homologous is understood as meaning identity or identical, respectively.

The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution, 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignments. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

Essential enzymic activity of the ω3-desaturase, Δ6-desaturase, Δ6-elongase, and/or Δ5-desaturase used in the process according to the invention means that they retain at least an enzymic activity of at least 10%, preferably 20%, particularly preferably 30% and very particularly 40% in comparison with the proteins/enzymes encoded by the sequence SEQ ID NO: 1, SEQ ID NO: 3, SEQ ID NO: 5, SEQ ID NO: 7 or SEQ ID NO: 9 and their derivatives and can therefore participate in the metabolism of compounds required for the synthesis of fatty acids, advantageously fatty esters such as phosphatidyl esters and/or triacylglyceride esters in a plant or a plant cell, or in the transport of molecules across membranes, meaning $C_{18}$- or $C_{20}$-carbon chains in the fatty acid molecule with double bonds in at least two, advantageously three or four, positions.

Nucleic acids which can advantageously be used in the process are derived from bacteria, fungi, diatoms, animals such as *Caenorhabditis* or *Oncorhynchus* or plants such as algae or mosses, such as the genera *Shewanella, Physcomitrella, Thraustochytrium, Fusarium, Phytophthora, Ceratodon, Pytium irregulare, Mantoniella, Ostreococcus, Isochrysis, Aleurita, Muscarioides, Mortierella, Borago, Phaeodactylum, Crypthecodinium*, specifically from the genera and species *Pytium irregulare, Oncorhynchus mykiss, Xenopus laevis, Ciona intestinalis, Thalassiosira pseudonona, Mantoniella squamata, Ostreococcus sp., Ostreococcus tauri, Euglena gracilis, Physcomitrella patens, Phytophthora infestans, Fusarium graminaeum, Cryptocodinium cohnii, Ceratodon purpureus, Isochrysis galbana, Aleurita farinosa, Thraustochytrium sp., Muscarioides viallii, Mortierella alpina, Borago officinalis, Phaeodactylum tricornutum, Caenorhabditis elegans* or especially advantageously from *Pytium irregulare, Thraustochytrium sp.* or *Thalassiosira pseudonana*.

Alternatively, nucleotide sequences which code for a Δ12-desaturase, Δ9-elongase, Δ8-desaturase, Δ5-elongase or Δ4-desaturase may also be used in the process according to the invention. The nucleic acid sequences used in the process are advantageously introduced into an expression cassette which enables said nucleic acids to be expressed in plants.

This involves functionally linking the nucleic acid sequences coding for Δ12-desaturase, ω3-desaturase, Δ9-elongase, Δ6-desaturase, Δ8-desaturase, Δ6-elongase, Δ5-desaturase, Δ5-elongase or Δ4-desaturase with one or more regulatory signals, advantageously for enhancing gene expression. Said regulatory sequences are intended to enable the genes and protein expression to be specifically expressed. Depending on the plant, this may mean, for example, that the gene is expressed and/or overexpressed only after induction or that it is expressed and/or overexpressed immediately. Advantageously, sequences are used for expression which enable constitutive expression in as many tissues of the plant as possible, such as the CaMV35S, CaMV36S, CaMV35Smas, nos, mas, ubi, stpt, lea or super promoter. Preference is given to expression in vegetative tissue, as described above. Said regulatory sequences are, for example, sequences to which inductors or repressors bind, regulating in this way expression of the nucleic acid. In addition to these novel regulatory sequences, or instead of these sequences, the natural regulation of these sequences may still be present upstream of the actual structural genes and may optionally have been genetically modified in such a way that said natural regulation has been eliminated and expression of the genes has been enhanced. Moreover, the gene construct may advantageously also comprise one or more "enhancer sequences" functionally linked to the promoter, which make possible enhanced expression of the nucleic acid sequence. Additional advantageous sequences such as further regulatory elements or terminator sequences may also be inserted at the 3' end of the DNA sequences, examples of advantageous terminator sequences being viral terminator sequences such as the 35S terminator sequence or others. The expression cassette (=gene construct) may comprise one or more copies of the enzymes, or nucleic acids coding for these enzymes, used in the process according to the invention. Advantageously, in each case only one copy of the genes is present in the expression cassette. This gene construct or the gene constructs may be introduced at the same time or successively into the plant and expressed together in the host organism. In this context, the gene construct(s) may be inserted in one or more vectors and be present in the cell in free form, or else be inserted in the genome. It is advantageous for the insertion of further genes into the plant, if the genes to be expressed are present together in a single gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

Advantageous regulatory sequences for the novel process are present for example in promoters such as the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. The process advantageously makes use of constitutive promoters. However, inducible promoters, such as the promoters described in EP-A-0 388 186 (benzenesulfonamide-inducible), Plant J. 2, 1992:397-404 (Gatz et al., tetracycline-inducible), EP-Δ0 335 528 (abscissic acid-inducible) or WO 93/21334 (ethanol- or cyclohexenol-inducible) may be employed in the process. Further suitable plant promoters are the cytosolic FBPase promoter or the ST-LSI promoter of potato (Stockhaus et al., EMBO J. 8, 1989, 2445), the *glycine max* phosphoribosylpyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very particularly advantageous are the abovementioned constitutive promoters, CaMV35S, CaMV36S, CaMV35Smas, nos, mas, ubi, stpt, lea, or the super promoter. In addition, it is also possible to use seed-specific promoters such as the USP (=unknown seed protein) promoter and the vicilin promoter (*Vicia faba*) [Bäumlein et al., Mol. Gen. Genet., 1991, 225(3)], the napin promoter (oilseed rape)

[U.S. Pat. No. 5,608,152], acyl carrier protein (oilseed rape) [U.S. Pat. No. 5,315,001 and WO 92/18634], the oleosin promoter (*Arabidopsis thaliana*) [WO 98/45461 and WO 93/20216], the phaseolin promoter (*Phaseolus vulgaris*) [U.S. Pat. No. 5,504,200], the Bce4 promoter [WO 91/13980], the leguminous B4 promoter (LegB4 promoter) [Bäumlein et al., Plant J., 2,2, 1992], Lpt2 and lpt1 (barley) [WO 95/15389 and WO 95/23230], seed-specific promoters from rice, corn and wheat [WO 99/16890], the Amy32b, Amy 6-6 and aleurain promoters [U.S. Pat. No. 5,677,474], Bce4 (oilseed rape) [U.S. Pat. No. 5,530,149], the glycinin promoter (soybean) [EP 571 741], the phosphoenol pyruvate carboxylase promoter (soybean) [JP 06/62870], ADR12-2 (soybean) [WO 98/08962], the isocitrate lyase promoter (oilseed rape) [U.S. Pat. No. 5,689,040] or α-amylase promoter (barley) [EP 781 849], but also other promoters such as the LeB4 promoter, DC3, phaseolin promoter or napin promoter. Further advantageous promoters are seed-specific promoters which can be used for monocotyledonous or dicotyledonous plants and which are described in U.S. Pat. No. 5,608,152 (oilseed rape napin promoter), WO 98/45461 (Arabidopsis oleosin promoter), U.S. Pat. No. 5,504,200 (*Phaseolus vulgaris* phaseolin promoter), WO 91/13980 (Brassica Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890.

In principle, it is possible to use all natural advantageously constitutive promoters together with their regulatory sequences, such as those mentioned above, for the novel process. It is also possible and advantageous to use synthetic promoters, either in addition or alone.

Plant gene expression can also be made possible via a chemically inducible promoter (see overview in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic acid-inducible promoter (WO 95/19443), a tetracycline-inducible promoter (Gatz et al. (1992) Plant J. 2, 397-404) and an ethanol-inducible promoter.

To ensure the stable integration of the biosynthesis genes into the transgenic plant over a plurality of generations, each of the nucleic acids which encode ω3-desaturase, Δ6-desaturase, Δ6-elongase, or Δ5-desaturase and which are used in the process should be expressed under the control of a separate promoter, which may advantageously be identical or different. Advantageously, different promoters are used since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and then, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to four times. To express the nucleic acid sequences, the latter are inserted behind the promoter via the suitable cleavage site, for example in the polylinker. Advantageously, each nucleic acid sequence has its own promoter and, if appropriate, its own terminator sequence (see FIG. 1). However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. In an advantageous embodiment, different promoters such as, for example, the USP, LegB4 or DC3 promoter, and different terminator sequences can be used in the expression cassette. In a further advantageous embodiment, identical promoters such as the CaMV35S promoter may also be used (see FIG. 1).

As described above, the transcription of the genes which have been introduced should advantageously be terminated by suitable terminator sequences at the 3' end of the biosynthesis genes which have been introduced (behind the stop codon). An example of a sequence which can be used in this context is the OCS1 terminator sequence. As is also the case with the promoters, different terminator sequences should be used for each gene.

As described above, the gene construct can also comprise further genes to be introduced into the organisms. It is possible and advantageous to introduce into the host plants, and to express therein, regulatory genes such as genes for inductors, repressors or enzymes which, owing to their enzyme activity, engage in the regulation of one or more genes of a biosynthetic pathway. These genes can be of heterologous or of homologous origin. Moreover, further biosynthesis genes of the fatty acid or lipid metabolism can advantageously be present in the nucleic acid construct, or gene construct; however, these genes can also be positioned on one or more further nucleic acid constructs. Biosynthesis genes of the fatty acid or lipid metabolism which are advantageously used is a gene selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) or combinations thereof. Especially advantageous nucleic acid sequences are biosynthesis genes of the fatty acid or lipid metabolism selected from the group of the acyl-CoA:lysophospholipid acyltransferase, Δ4-desaturase, Δ8-desaturase, Δ9-desaturase, Δ12-desaturase, Δ5-elongase and/or Δ9-elongase.

In this context, the abovementioned nucleic acids or genes can be cloned into expression cassettes, like those mentioned above, in combination with other elongases and desaturases and used for transforming plants with the aid of *Agrobacterium*.

The term "vector" used in the present specification means a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacteria vectors with bacterial replication origin). Other vectors are advantageously integrated into the genome of a host cell when they are introduced into the host cell, and thus replicate together with the host genome. Moreover, certain vectors can govern the expression of genes with which they are functionally linked. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is also intended to comprise other forms of expression vectors, such as viral vectors, which exert similar functions. Furthermore, the term "vector" is also intended to comprise other vectors with which the skilled worker is familiar, such as phages, viruses such as SV40, CMV, TMV, transposons, IS elements, plasmids, phagemids, cosmids, linear or circular DNA.

The recombinant expression vectors advantageously used in the process comprise the nucleic acid sequences used in the process or the above-described gene construct in a form which is suitable for expressing the nucleic acids used in a host cell, which means that the recombinant expression vectors comprise one or more regulatory sequences, selected on the basis of the host cells to be used for the expression, which regulatory sequence(s) is/are functionally linked with the nucleic acid sequence to be expressed. In a recombinant expression vector, "functionally linked" means that the nucleotide sequence of interest is bound to the regulatory sequence(s) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the expression level of the desired protein and the like.

The recombinant expression vectors used can be designed for the expression of the nucleic acid sequences used in the process in such a way that they can be transformed into prokaryotic intermediate hosts and ultimately, after having been introduced into the plants, permit expression therein. This is advantageous since intermediate steps of the vector construction are frequently carried out in microorganisms for the sake of simplicity. For example, the ω3-desaturase, Δ6-desaturase, Δ6-elongase and/or Δ5-desaturase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi," in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates, using vectors in a transformation method as described in WO 98/01572 and, preferably, in cells of multi-celled plants (see Schmidt, R. and Willmitzer, L. (1988) "High efficiency Agrobacterium tumefaciens-mediated transformation of Arabidopsis thaliana leaf and cotyledon explants" Plant Cell Rep.:583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E-binding protein and protein A, respectively, is fused with the recombinant target protein.

Examples of suitable inducible nonfusion E. coli expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example in E. coli pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCl, in Streptomyces pIJ101, pIJ364, pIJ702 or pIJ361, in Bacillus pUB110, pC194 or pBD214, in Corynebacterium pSA77 or pAJ667.

In a further embodiment, the expression vector is a yeast expression vector. Examples for vectors for expression in the yeast S. cerevisiae comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi", in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, the nucleic acid sequences used in the process according to the invention can be expressed in insect cells using Baculovirus expression vectors. Baculovirus vectors which are available for the expression of proteins in cultured insect cells (for example Sf9 cells) comprise the pAc series (Smith et al. (1983) Mol. Cell. Biol. 3:2156-2165) and the pVL series (Lucklow and Summers (1989) Virology 170: 31-39).

The abovementioned vectors are only a small overview over suitable vectors which are possible. Further plasmids are known to the skilled worker and are described, for example, in: Cloning Vectors (Ed. Pouwels, P. H., et al., Elsevier, Amsterdam-N.Y.-Oxford, 1985, ISBN 0 444 904018). For further suitable expression systems for prokaryotic and eukaryotic cells, see the Chapters 16 and 17 in Sambrook, J., Fritsch, E. F., and Maniatis, T., Molecular Cloning: A Laboratory Manual, 2nd edition, Cold Spring Harbor Laboratory, Cold Spring Harbor Laboratory Press, Cold Spring Harbor, N.Y., 1989.

The gene used in the process can also be expressed in single-celled plant cells (such as algae), see Falciatore et al., 1999, Marine Biotechnology 1 (3):239-251 and references cited therein, and in plant cells from higher plants (for example spermatophytes such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, pp. 15-38.

A plant expression cassette preferably comprises regulatory sequences which are capable of governing the expression of genes in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminators which are functionally active in plants are also suitable.

Since plant gene expression is very often not limited to the transcriptional level, a plant expression cassette preferably comprises other sequences which are functionally linked, such as translation enhancers, for example the overdrive sequence, which comprises the tobacco mosaic virus 5'-untranslated leader sequence, which increases the protein/RNA ratio (Gallie et al., 1987, Nucl. Acids Research 15:8693-8711).

As described above, plant gene expression must be functionally linked with a suitable promoter which triggers gene expression with the correct timing or in a cell- or tissue-specific manner. Advantageously utilizable promoters are constitutive promoters (Benfey et al., EMBO J. 8 (1989) 2195-2202), such as those which are derived from plant viruses, such as 35S CaMV (Franck et al., Cell 21 (1980) 285-294), 19S CaMV (see also U.S. Pat. No. 5,352,605 and WO 84/02913), or plant promoters, such as the promoter of the small Rubisco subunit, which is described in U.S. Pat. No. 4,962,028.

Other preferred sequences for use in functional linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmic reticulum, elaioplasts, peroxisomes and other compartments of plant cells.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

In particular, it may be desired to bring about the multiparallel expression of the ω3-desaturases, Δ6-desaturases, Δ6-elongases, and/or Δ5-desaturases used in the process. Such expression cassettes can be introduced via the simultaneous transformation of a plurality of individual expression constructs or, preferably, by combining a plurality of expression cassettes on one construct. Also, a plurality of vectors can be transformed with in each case a plurality of expression cassettes and then transferred into the host cell.

Other promoters which are likewise especially suitable are those which bring about a plastid-specific expression, since plastids constitute the compartment in which the precursors and some end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

Vector DNA can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

In an advantageous embodiment, the term "nucleic acid (molecule)" as used in the present context additionally comprises the untranslated sequence at the 3' and at the 5' end of the coding gene region: at least 500, preferably 200, especially preferably 100 nucleotides of the sequence upstream of the 5' end of the coding region and at least 100, preferably 50, especially preferably 20 nucleotides of the sequence downstream of the 3' end of the coding gene region. An "isolated" nucleic acid molecule is separated from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' ends of the nucleic acid). In various embodiments, the isolated ω3-desaturase, Δ6-desaturase, Δ6-elongase, or Δ5-desaturase molecule used in the process can comprise for example fewer than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived.

The nucleic acid molecules used in the process can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe and standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for isolating further nucleic acid sequences which can be used in the process. Moreover, the nucleic acid molecules used in the process or parts thereof can be isolated by polymerase chain reaction, where oligonucleotide primers which are on the basis of this sequence or of parts thereof are used (for example a nucleic acid molecule comprising the complete sequence or part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for the amplification by means of polymerase chain reaction can be generated based on one of the sequences shown in SEQ ID NO: 1, SEQ ID NO: 3, SEQ ID NO:5, SEQ ID NO: 7 or SEQ ID NO: 9 or with the aid of the amino acid sequences detailed in SEQ ID NO: 2, SEQ ID NO: 4, SEQ ID NO:6, SEQ ID NO: 8 or SEQ ID NO: 10. A nucleic acid according to the invention can be amplified by standard PCR amplification techniques using cDNA or, alternatively, genomic DNA as template and suitable oligonucleotide primers. The nucleic acid thus amplified can be cloned into a suitable vector and characterized by means of DNA sequence analysis. Oligonucleotides which correspond to a desaturase nucleotide sequence can be generated by standard synthetic methods, for example using an automatic DNA synthesizer.

Homologs of the used ω3-desaturase, Δ6-desaturase, Δ6-elongase, or Δ5-desaturase nucleic acid sequences with the sequence SEQ ID NO: 1, SEQ ID NO: 3, SEQ ID NO:5, SEQ ID NO: 7 or SEQ ID NO: 9, means, for example, allelic variants with at least approximately 40, 50 or 60%, preferably at least approximately 60 or 70%, more preferably at least approximately 70 or 80%, 90% or 95% and even more preferably at least approximately 85%, 86%, 87%, 88%, 89%, 90%, 91%, 92%, 93%, 94%, 95%, 96%, 97%, 98%, 99% or more identity or homology with a nucleotide sequences shown in SEQ ID NO: 1, SEQ ID NO: 3, SEQ ID NO:5, SEQ ID NO: 7 or SEQ ID NO: 9, or its homologs, derivatives or analogs or parts thereof. Furthermore, isolated nucleic acid molecules of a nucleotide sequence which hybridize with one of the nucleotide sequences shown in SEQ ID NO: 1, SEQ ID NO: 3, SEQ ID NO:5, SEQ ID NO: 7 or SEQ ID NO: 9, or with a part thereof, are for example hybridized under stringent conditions. A part thereof is understood as meaning, in accordance with the invention, that at least 25 base pairs (=bp), 50 bp, 75 bp, 100 bp, 125 bp or 150 bp, preferably at least 175 bp, 200 bp, 225 bp, 250 bp, 275 bp or 300 bp, especially preferably 350 bp, 400 bp, 450 bp, 500 bp or more base pairs are used for the hybridization. It is also possible and advantageous to use the full sequence. Allelic variants comprise in particular functional variants which can be obtained by deletion, insertion or substitution of nucleotides from the sequence detailed in SEQ ID NO: 1, SEQ ID NO: 3, SEQ ID NO:5, SEQ ID NO: 7 or SEQ ID NO: 9, it being intended, however, that the enzyme activity of the resulting proteins which are synthesized is advantageously retained for the insertion of one or more genes. Proteins which retain the enzymatic activity of ω3-desaturase, Δ6-desaturase, Δ6-elongase, and/or Δ5-desaturase, i.e. whose activity is essentially not reduced, means proteins with at least 10%, preferably 20%, especially preferably 30%, very especially preferably 40% of the original enzyme activity in comparison with the protein encoded by SEQ ID NO: 2, SEQ ID NO: 4, SEQ ID NO:6, SEQ ID NO: 8 or SEQ ID NO: 10. The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution, 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignments. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

Lipid synthesis can be divided into two sections: the synthesis of fatty acids and their binding to sn-glycerol-3-phosphate, and the addition or modification of a polar head group such as the phosphatidyl residue. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydration reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, N.Y., and the references therein, and Magnuson, K., et al. (1993) Microbiological Reviews 57:522-542 and the references therein). To undergo the further elongation steps, the resulting phospholipid-bound fatty acids must be returned from the phospholipids to the fatty acid CoA ester pool. This is made possible by acyl-CoA:lysophospholipid acyltransferases. Moreover, these enzymes are capable of transferring the elongated fatty acids from the CoA esters back to the phospholipids. If appropriate, this reaction sequence can be followed repeatedly.

Examples of precursors for the biosynthesis of PUFAs are oleic acid, linoleic acid and linolenic acid. These $C_{18}$-carbon fatty acids must be elongated to $C_{20}$ fatty acids in order to obtain ARA and EPA. With the aid of the desaturases used in the process, such as the ω3-, Δ5- and Δ6-desaturases and/or Δ6-elongases, arachidonic acid and/or eicosapentaenoic acid can be produced and subsequently employed in various applications regarding foodstuffs, feedstuffs, cosmetics or pharmaceuticals. $C_{20}$ fatty acids with at least two, advantageously at least three, four or five, double bonds in the fatty acid molecule, preferably $C_{20}$-fatty acids with advantageously four or five double bonds in the fatty acid molecule, can be prepared using the abovementioned enzymes. Desaturation may take place before or after elongation of the fatty acid in question. This is why the products of the desaturase activities and the further desaturation and elongation steps which are possible result in preferred PUFAs with a higher degree of desaturation to fatty acids such as γ-linolenic acid, dihomo-γ-linolenic acid, arachidonic acid, stearidonic acid, eicosatetraenoic acid or eicosapentaenoic acid. Substrates of the desaturases and elongases used in the process according to the invention are $C_{16}$- or $C_{18}$ fatty acids such as, for example, linoleic acid, γ-linolenic acid, α-linolenic acid, dihomo-γ-linolenic acid, eicosatetraenoic acid or stearidonic acid. Preferred substrates are oleic acid, linoleic acid, γ-linolenic acid and/or α-linolenic acid. The synthesized $C_{20}$ fatty acids with at least two, three, four or five double bonds in the fatty acids are obtained in the process according to the invention in the form of the free fatty acid or advantageously in the form of their esters, for example in the form of their glycerides or phospholipids.

The term "glyceride" is understood as meaning glycerol esterified with one, two or three carboxyl radicals (mono-, di- or triglyceride). "Glyceride" is also understood as meaning a mixture of various glycerides. The glyceride is advantageously the triglyceride. The glyceride or glyceride mixture may comprise further additions, for example free fatty acids, antioxidants, proteins, carbohydrates, vitamins and/or other substances.

For the purposes of the process according to the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the advantageous triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

For publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of producing themselves in sufficient quantity and must therefore take up additional quantities, although they can be synthesized readily by other organisms such as bacteria; for example, cats are no longer capable of synthesizing arachidonic acid.

Phospholipids for the purposes of the invention are understood as meaning phosphatidylcholine, phosphatidylethanolamine, phosphatidylserine, phosphatidylglycerol and/or phosphatidylinositol, advantageously phosphatidylcholine and/or phosphatidylserine. The terms production or productivity are known in the art and encompass the productivity within a plant cell or a plant, that is to say the content of the desired fatty acids produced in the process based on the content of all fatty acids in this cell or plant. The term production efficiency comprises the time required for obtaining a specific production quantity (for example the time required by the cell to establish a certain throughput rate of a fine chemical). The terms biosynthesis or biosynthetic pathway are known in the art and comprise the synthesis of a compound, preferably an organic compound, by a cell from intermediates, for example in a multi-step and strongly regulated process. The terms catabolism or catabolic pathway are known in the art and comprise the cleavage of a compound, preferably of an organic compound, by a cell to give catabolites (in more general terms, smaller or less complex molecules), for example in a multi-step and strongly regulated process. The term metabolism is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

Owing to their homology to the ω3-desaturase, Δ6-desaturase, Δ5-desaturase, and/or Δ6-elongase nucleic acids disclosed here, nucleic acid molecules which are advantageous for the process according to the invention can be isolated following standard hybridization techniques under stringent hybridization conditions, using the sequences or part thereof as hybridization probe. In this context it is possible, for example, to use isolated nucleic acid molecules which are at least 15 nucleotides in length and which hybridize under stringent conditions with the nucleic acid molecules which comprise a nucleotide sequence of SEQ ID NO: 1, SEQ ID NO: 3, SEQ ID NO: 5, SEQ ID NO: 7 or SEQ ID NO: 9. Nucleic acids with at least 25, 50,100, 250 or more nucleotides can also be used. The term "hybridizes under stringent conditions" as used in the present context is intended to describe hybridization and washing conditions under which nucleotide sequences with at least 60% homology to one another usually remain hybridized with one another. Conditions are preferably such that sequences with at least approximately 65%, preferably at least approximately 70% and especially preferably at least 75% or more homology to one another usually remain hybridized to one another. These stringent conditions are known to the skilled worker and described, for example, in Current Protocols in Molecular Biology, John Wiley & Sons, N.Y. (1989), 6.3.1-6.3.6. A preferred nonlimiting example of stringent hybridization conditions is hybridizations in 6× sodium chloride/sodium citrate (=SSC) at approximately 45° C., followed by one or more washing steps in 0.2×SSC, 0.1% SDS at 50 to 65° C. The skilled worker knows that these hybridization conditions differ depending on the type of nucleic acid and, for example when organic solvents are present, regarding temperature and buffer concentration. Under "standard hybridization conditions", for example, the temperature is, depending on the type of nucleic acid, between 42° C. and 58° C. in aqueous buffer with a concentration of 0.1 to 5×SSC (pH 7.2). If an organic solvent, for example 50% formamide, is present in the abovementioned buffer, the temperature under standard conditions is approximately 42° C. The hybridization conditions for DNA:DNA hybrids, for example, are preferably 0.1×SSC and 20° C. to 45° C., preferably 30° C. to 45° C. The hybridization conditions for DNA:RNA hybrids are, for example, preferably 0.1×SSC and 30° C. to 55° C., preferably 45° C. to 55° C. The abovementioned hybridization temperatures are determined by way of example for a nucleic acid with approximately 100 bp (=base pairs) in length and with a G+C content of 50% in the absence of formamide. The skilled worker knows how to determine the required hybridization conditions on the basis of the abovementioned textbooks or textbooks such as Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

In order to determine the percentage of homology (=identity) of two amino acid sequences (for example one of the sequences of SEQ ID NO: 2, SEQ ID NO: 4, SEQ ID NO: 6, SEQ ID NO: 8 or SEQ ID NO: 10) or of two nucleic acids (for example SEQ ID NO: 1, SEQ ID NO: 3, SEQ ID NO: 5, SEQ ID NO: 7 or SEQ ID NO: 9) the sequences are written one under the other for an optimal comparison (for example, gaps may be introduced into the sequence of a protein or of a nucleic acid in order to generate an optimal alignment with the other protein or the other nucleic acid). Then, the amino acid residues or nucleotides at the corresponding amino acid positions or nucleotide positions are compared. If a position in a sequence is occupied by the same amino acid residue or the same nucleotide as the corresponding position in the other sequence, then the molecules are homologous at this position (i.e. amino acid or nucleic acid "homology" as used in the present context corresponds to amino acid or nucleic acid "identity"). The percentage of homology between the two sequences is a function of the number of identical positions which the sequences share (i.e. % homology=number of identical positions/total number of positions ×100). The terms homology and identity are therefore to be considered as synonymous. The programs and algorithms used are those described above.

An isolated nucleic acid molecule which encodes a ω3-desaturase, Δ6-desaturase, Δ5-desaturase, and/or Δ6-elongase used in the process which is homologous to a protein sequence of SEQ ID NO: 2, SEQ ID NO: 4, SEQ ID NO: 6, SEQ ID NO: 8 or SEQ ID NO: 10 can be generated by introducing one or more nucleotide substitutions, additions or deletions in/into a nucleotide sequence of SEQ ID NO: 1, SEQ ID NO: 3, SEQ ID NO: 5, SEQ ID NO: 7 or SEQ ID NO: 9 so that one or more amino acid substitutions, additions or deletions are introduced in/into the protein which is encoded. Mutations in one of the sequences of SEQ ID NO: 1, SEQ ID NO: 3, SEQ ID NO: 5, SEQ ID NO: 7 or SEQ ID NO: 9 can be introduced by standard techniques such as site-specific mutagenesis and PCR-mediated mutagenesis. It is preferred to generate conservative amino acid substitutions in one or more of the predicted nonessential amino acid residues. In a "conservative amino acid substitution", the amino acid residue is replaced by an amino acid residue with a similar side chain. Families of amino acid residues with similar side chains have been defined in the art. These families comprise amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in a ω3-desaturase, Δ6-desaturase, Δ5-desaturase, and/or Δ6-elongase is thus preferably replaced by another amino acid residue from the same family of side chains. In another embodiment, the mutations can, alternatively, be introduced randomly over all or part of the sequence encoding the ω3-desaturase, Δ6-desaturase, Δ5-desaturase, and/or Δ6-elongase, for example by saturation mutagenesis, and the resulting mutants can be screened by recombinant expression for the herein-described ω3-desaturase, Δ6-desaturase, Δ5-desaturase, or Δ6-elongase activity in order to identify mutants which have retained the ω3-desaturase, Δ6-desaturase, Δ5-desaturase, and/or Δ6-elongase activity. Following the mutagenesis, the protein which is encoded can be expressed recombinantly, and the activity of the protein can be determined, for example using the tests described in the present text.

The present invention is illustrated in greater detail by the examples which follow, which are not to be construed as limiting. The content of all of the references, patent applications, patents and published patent applications cited in the present patent application is herewith incorporated by reference.

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the method of Sanger (Sanger et al. (1977) Proc. Natl. Acad. Sci. USA 74, 5463-5467). Fragments obtained by polymerase chain reaction were sequenced and verified to avoid polymerase errors in constructs to be expressed.

Example 3

Cloning of Expression Plasmids for Expression in Plants

To transform plants, transformation vectors were generated on the basis of pGPTV-35S, a plasmid based on pBIN19-35S (Bevan M. (1984) Binary *Agrobacterium* vectors for plant transformation. Nucl. Acids Res. 18:203). For this purpose, an expression cassette comprising the promoter element CaMV35S (SEQ ID NO: 11) and the 35S terminator sequence (SEQ ID NO: 12; Franck, A., Guilley, H., Jonard, G., Richards, K. and Hirth, L. (1980) Nucleotide sequence of cauliflower mosaic virus DNA Cell 21 (1), 285-294) was assembled in a pUC vector. The promoter was inserted here via the SalI/XbaI restriction cleavage sites and the terminator sequence was inserted via BamHI/SmaI. This involved attaching a polylinker having the XhoI cleavage site to the terminator sequence ('triple ligation'). The resulting plasmid, pUC19-35S, was then used for cloning PUFA genes. The open reading frames of the d6Des(Pir, SEQ ID NO: 1), d5Des (Tc, SEQ ID NO: 5) and d6Elo(Tc, SEQ ID NO: 3) sequences were introduced in parallel via EcoRV into pUC19-35S vectors. The resulting plasmids, pUC-D6, pUC-D5, pUC-E6 (Tc), were used for producing the binary vector, pGPTV-35S_D6D5E6(Tc). For this purpose, the pGPTV vector was digested with the enzyme SalI, the pUC-D6 plasmid was digested with SalI/XhoI, and the correct fragments were ligated. The resulting plasmid, pGPTV-D6, was subsequently digested with SalI, the pUC-D5 plasmid was digested with SalI/XhoI, and the correct fragments were ligated. The resulting plasmid, pGPTV-D6-D5, was then digested once more with SalI, the pUC-E6(Tc) plasmid was digested with SalI/XhoI, and the correct fragments were ligated. These sequential cloning steps produced the binary vector, pGPTV-D6D5E6(Tc), which was used for transformation.

In a further embodiment, the sequence of d6Elo(Tp) [SEQ ID NO: 7] rather than the sequence d6Elo(Tc) was inserted into the pUC19-35S vector. The resulting plasmid, pUC-E6 (Tp), was used for preparing the binary vector, pGPTV-35S_D6D5E6(Tp). In a further embodiment, the open reading frame of ω3Des(Pi, SEQ ID NO: 9) was cloned into pUC19-35S. The resulting plasmid, pUC-ω3Pi, was transferred via SalI/XhoI into the binary vectors, pGPTV-D6D5E6 (Tc) and pGPTV-D6D5E6(Tp). The resulting vectors, pGPTV-D6D5E5(Tc)ω3Pi and pGPTV-D6D5E5(Tp)ω3Pi, were used for plant transformation.

FIG. 1 gives an overview over the constructs produced.

All binary vectors were transformed into *E. coli* DH5α cells (Invitrogen) according to the manufacturer's information. Positive clones were identified by PCR and plasmid DNA was isolated (Qiagen Dneasy).

Composition of the PCR mix (50 µL):
5.00 µL of cDNA template
5.00 µL of 10× buffer (Advantage polymerase)+25 mM $MgCl_2$
5.00 µL of 2 mM dNTP
1.25 µL of each primer (10 pmol/µL)
0.50 µL of Advantage polymerase The Advantage polymerase from Clontech was used.

The vectors were checked and then transformed by means of electroporation into *Agrobacterium tumefaciens* GC3101 and plated on agar plates containing 2% YEB medium+kanamycin. Kanamycin-tolerant cells were selected and used for transformation of *Brassica juncea* and *Arabidopsis thaliana* or can be used for transforming other plant species.

Example 4

Generation of Transgenic Plants a) Generation of transgenic oilseed rape plants (*Brassica juncea*, modified according to Radke et al., Transformation and regeneration of *Brassica rapa* using *Agrobacterium tumefaciens*. Plant Cell Rep. 11, 499-505, 1992).

Transgenic oilseed rape plants are generated by transforming binary vectors such as the binary plasmids/vectors generated in Example 3 into *Agrobacterium tumefaciens* GC3101 (Deblaere et al, 1984, Nucl. Acids. Res. 13, 4777-4788). To transform oilseed rape plants (Var. *Drakkar*, NPZ Nordeutsche Pflanzenzucht, Hohenlieth, Germany), a 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) is used. Petioles or hypocotyls of freshly germinated sterile oilseed rape plants (in each case approx. 1 cm$^2$) were incubated with a 1:50 agrobacterial dilution in a Petri dish for 5-10 minutes. This is followed by 3 days of coincubation in the dark at 25° C. on 3MS medium supplemented with 0.8% Bacto agar. Culturing was continued after 3 days at 16 hours of light/8 hours of darkness, and continued in a weekly rhythm on MS medium supplemented with 500 mg/l Claforan (Cefotaxime sodium), 50 mg/l kanamycin, 20 microM benzylaminopurine (BAP) and 1.6 g/l glucose. Growing shoots were transferred to MS medium supplemented with 2% sucrose, 250 mg/l Claforan and 0.8% Bacto agar. If no roots had developed after three weeks, 2-indolebutyric acid was added to the medium as growth hormone for rooting.

Regenerated shoots were obtained on 2MS medium supplemented with kanamycin and Claforan; after rooting, they were transferred to soil and, after culturing, grown in a controlled-environment cabinet or in the greenhouse for two weeks, allowed to flower, and mature seeds were harvested and analyzed by means of lipid analyses for expression of the desaturase and elongase genes, as described by way of example in Qiu et al. 2001, J. Biol. Chem. 276, 31561-31566.

b) Generation of transgenic linseed plants

Transgenic linseed plants may be produced, for example, by the method of Bell et al., 1999, In Vitro Cell. Dev. Biol.-Plant. 35(6):456-465 by means of particle bombardment. *Agrobacteria*-mediated transformations may be established, for example, according to Mlynarova et al. (1994), Plant Cell Report 13: 282-285 or Drexler et al. (2003), Mol. Breeding 11, 149-158.

Example 5

Lipid Extraction from *Brassica juncea* and *Arabidopsis thaliana* Leaves

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of the desired product (i.e. of the lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research", Oxford: Pergamon Press, 1 (1952)-16 (1977) under the title: Progress in the Chemistry of Fats and Other Lipids CODEN.

One example is the analysis of fatty acids (abbreviations: FAME, fatty acid methyl ester; GC-MS, gas liquid chromatography/mass spectrometry; TAG, triacylglycerol; TLC, thin-layer chromatography).

The unambiguous detection for the presence of fatty acid products can be obtained by analyzing recombinant organisms using standard analytical methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometry methods], Lipids 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 μm, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

To analyze transgenic *Brassica juncea* and *Arabidopsis thaliana* plants, the plant material was initially homogenized mechanically by comminuting in a pestle and mortar to make it more amenable to extraction. This was followed by heating at 100° C. for 10 minutes and, after cooling on ice, by resedimentation. The cell sediment was hydrolyzed for one hour at 90° C. with 1 M methanolic sulfuric acid and 2% dimethoxypropane, and the lipids were transmethylated. The resulting fatty acid methyl esters (FAMEs) were extracted in petroleum ether. The extracted FAMEs were analyzed by gas liquid chromatography using a capillary column (Chrompack, WCOT Fused Silica, CP-Wax-52 CB, 25 m, 0.32 mm) and a temperature gradient of from 170° C. to 240° C. in 20 minutes and 5 minutes at 240° C. The identity of the fatty acid methyl esters was confirmed by comparison with corresponding FAME standards (Sigma). The identity and position of the double bond can be analyzed further by suitable chemical derivatization of the FAME mixtures, for example to give 4,4-dimethoxyoxazoline derivatives (Christie, 1998) by means of GC-MS.

Analysis of leaf material of transgenic *Brassica juncea* plants with the pGPTV-D6D5E6(Tc) construct:

Plants which had been transformed with the pGPTV-D6D5E6(Tc) plasmid according to Example 4 were examined for modified fatty acids. Leaves which were extracted according to the description above and analyzed by gas chromatography were used as starting material.

The transgenic plants were shown here to be able to produce new fatty acids (Table 1, comparison with control). Table 1 can be found at the end of the specification. The analysis of numerous independent transgenic lines indicated that the fatty acids GLA (γ18:3), SDA (18:4), DGLA (20:3d8, 11,14), AA (20:4) and EPA (20:5) were generated in the leaf material due to the activity of the genes employed. Said fatty acids are not present in untransformed plants ('control'). Arachidonic acid (AA) and eicosapentaenoic acid (EPA) are in this context valuable fatty acids for human nutrition. Up to 8.9% and 4.8%, respectively, of these two valuable fatty acids are present.

EPA is a particularly valuable fatty acid. For this reason, attempts at increasing the EPA content were carried out. A first approach consisted of the use of an ARA-specific ω3-desaturase which converts ARA to EPA. In a further approach, the use of an 18:4-specific elongase in combination with said ω3-desaturase was tested.

Analysis of leaf material of transgenic *Brassica juncea* plants with the pGPTV-D6D5E6(Tc)ω3Pi construct:

Plants which had been transformed with the pGPTV-D6D5E6(Tc)ω3Pi plasmid according to Example 4 were examined for modified fatty acids. Leaves which were extracted according to the description above and analyzed by gas chromatography were used as starting material.

The transgenic plants were shown here to be able to produce new fatty acids (Table 2, comparison with control). Table 2 can be found at the end of the specification. The analysis of numerous independent transgenic lines indicated that the fatty acids GLA (γ18:3), SDA (18:4), 20:4d8,11,14, 17 and EPA (20:5) were generated in the leaf material due to the activity of the genes employed. Said fatty acids are not present in untransformed plants ('control'). Eicosapentaenoic acid (EPA) is in this context a valuable fatty acid for human nutrition. Up to 12.5% of this valuable fatty acid are present. The additional use of ω3Pi here clearly reduces the M content and shifts the reaction in the direction of the more valuable product, EPA.

Analysis of leaf material of transgenic *Brassica juncea* plants with the pGPTV-D6D5E6(Tp)ω3Pi construct:

Plants which had been transformed with the pGPTV-D6D5E6(Tp)ω3Pi plasmid according to Example 4 were examined for modified fatty acids. Leaves which were extracted according to the description above and analyzed by gas chromatography were used as starting material.

The transgenic plants were shown here to be able to produce new fatty acids (Table 3, comparison with control). Table 3 can be found at the end of the specification. The analysis of numerous independent transgenic lines indicated that the fatty acids GLA (γ18:3), SDA (18:4), 20:4d8,11,14, 17 and EPA (20:5) were generated in the leaf material due to the activity of the genes employed. Said fatty acids are not present in untransformed plants ('control'). Eicosapentaenoic acid (EPA) is in this context a valuable fatty acid for human nutrition. Up to 14.7% of this valuable fatty acid are present. The additional use of ω3Pi here clearly reduces the ARA content and shifts the reaction in the direction of the more valuable product, EPA. Higher EPA (20:5) contents were achieved in comparison with the pGPTV-D6D5E6(Tc)ω3Pi construct.

In this context, the synthesis of the valuable fatty acid, EPA (20:5), was shown to take place preferably in leaves (Table 4). In the other plant organs, seeds, stalk and flower, only very low amounts of EPA and the precursors can be detected.

A further embodiment investigated whether the valuable fatty acid, EPA, is enriched in a particular lipid class or particular lipid classes. For this purpose, the total lipid was extracted from leaves, as described above, and then fractionated into neutral and polar lipids by means of a silicate PrepSep column (Fisher Scientific, USA). In a further step, the neutral lipid fraction was fractionated by means of thin layer chromatography (G-25, Machery-Nagel) the triacylglycerides (hexane/diethyl ether/acetic acid 70:30:1, vol/vol/vol). Aliquots of the polar lipid fraction were fractionated with chloroform/methanol/ammonia (65:25:4, vol/vol/vol/, galactolipids) or with chloroform/methanol/ammonia/water (70:30:4:1, vol/vol/vol/vol, phospholipids). The individual lipid classes were identified under UV light, after spraying with Primuline solution (0.05% in 80% acetone, Sigma) and scraped off the thin layer plate and transmethylated for gas-chromatographic analysis, as described hereinabove.

Table 5 depicts the results of this analysis in the various lipid classes. Table 5 can be found at the end of the description. A distinct enrichment of EPA in TAG, the oil fraction, was found. Furthermore, an accumulation in phosphatidyl-choline (PC) and phosphatidylserine was observed in the polar fraction.

TABLE 1

Gas-chromatographic analysis of fatty acids from leaf material of Brassica juncea plants transformed with the pGPTV-D6D5E6(Tc) plasmid. The measurement indicates the percentage of the individual fatty acids in the various transgenic lines.

| Fatty acid | 16:0 | 16:1 | 16:3 | 18:0 | 18:1 (n-9) | 18:1 (n-11) | 18:2 | 18:3 (GLA) | 18:3 (ALA) | 18:4 (SDA) | DGLA | ARA | EPA |
|---|---|---|---|---|---|---|---|---|---|---|---|---|---|
| Control PGPTV-D6D5E6(Tc) | 11.2 | 1.8 | 13.2 | 1.4 | 0.6 | 0.8 | 6.4 | 0.0 | 55.9 | 0.0 | 0.0 | 0.0 | 0.0 |
| C23-1 | 13.5 | 1.4 | 10.8 | 2.5 | 1.5 | 1.2 | 6.8 | 9.1 | 31.2 | 7.1 | 0.3 | 2.4 | 1.7 |
| C23-2 | 15.3 | 1.7 | 11.8 | 3.0 | 2.1 | 1.1 | 4.1 | 5.2 | 21.9 | 4.0 | 2.1 | 8.8 | 4.8 |
| C23-3 | 14.7 | 1.4 | 11.4 | 2.5 | 1.5 | 0.9 | 6.1 | 10.4 | 26.5 | 7.4 | 0.4 | 2.8 | 1.8 |
| C23-4 | 13.0 | 2.0 | 13.8 | 1.8 | 0.5 | 1.1 | 5.6 | 6.2 | 39.3 | 5.5 | 0.3 | 1.8 | 1.3 |
| C23-5 | 18.9 | 2.8 | 10.4 | 3.2 | 1.9 | 1.5 | 4.2 | 6.0 | 18.9 | 3.4 | 1.7 | 8.9 | 4.2 |
| C23-6 | 13.6 | 1.8 | 11.7 | 2.3 | 1.2 | 1.3 | 8.1 | 9.1 | 33.1 | 5.8 | 0.3 | 1.3 | 0.9 |
| C23-7 | 14.5 | 1.2 | 10.8 | 3.1 | 1.7 | 1.3 | 7.8 | 9.7 | 27.4 | 6.0 | 0.5 | 3.3 | 2.2 |
| C23-9 | 15.2 | 1.9 | 12.9 | 2.4 | 1.3 | 1.3 | 3.8 | 6.8 | 25.6 | 4.5 | 1.3 | 8.4 | 4.8 |

TABLE 2

Gas-chromatographic analysis of fatty acids from leaf material of Brassica juncea plants transformed with the pGPTV-D6D5E6(Tc)ω3Pi plasmid. The measurement indicates the percentage of individual fatty acids in the non-transgenic control (Wt) and the various transgenic lines.

| Fatty acid | 16:0 | 16:1 | 16:2 | 16:3 | 18:0 | 18:1 (n-9) | 18:1 (n-11) | 18:2 LA | 18:3 (GLA) | 18:3 (ALA) | 18:4 (SDA) | HGLA 20:3 c8, 11, 14 | ARA | 20:4 c8, 1, 14, 17 | EPA |
|---|---|---|---|---|---|---|---|---|---|---|---|---|---|---|---|
| Wt | 12.73 | 2.14 | 0.49 | 14.34 | 1.07 | 0.93 | 0.70 | 11.79 | — | 52.28 | — | — | n.d. | — | — |
| 11-3 | 15.69 | 1.18 | 0.80 | 13.69 | 1.97 | 2.83 | 0.61 | 3.86 | 6.68 | 24.01 | 7.24 | — | n.d. | 1.91 | 12.48 |
| 11-5 | 13.51 | 1.67 | 0.59 | 14.23 | 1.49 | 1.41 | 0.75 | 5.01 | 5.53 | 34.04 | 5.74 | — | n.d. | 1.32 | 9.21 |
| 11-13 | 12.46 | 1.47 | 0.60 | 14.06 | 1.27 | 1.41 | 0.80 | 6.97 | 3.77 | 37.82 | 4.82 | — | n.d. | 0.63 | 8.25 |

TABLE 3

Gas-chromatographic analysis of fatty acids from leaf material of Brassica juncea plants transformed with the pGPTV D6D5E6(Tp)ω3Pi plasmid. The measurement indicates the percentage of individual fatty acids in the non-transgenic control (Wt) and the various transgenic lines.

| Fatty acid | 16:0 | 16:1 | 16:2 | 16:3 | 18:0 | 18:1 (n-9) | 18:1 (n-11) | 18:2 LA | 18:3 (GLA) | 18:3 (ALA) | 18:4 (SDA) | HGLA 20:3 c8, 11, 14 | ARA | 20:4 c8, 1, 14, 17 | EPA |
|---|---|---|---|---|---|---|---|---|---|---|---|---|---|---|---|
| Wt | 12.73 | 2.14 | 0.49 | 14.34 | 1.07 | 0.93 | 0.70 | 11.79 | — | — | — | — | — | — | — |
| 10-6 | 15.04 | 1.32 | 0.68 | 11.15 | 1.70 | 2.20 | 0.63 | 4.00 | 4.95 | 25.47 | 4.38 | 0.59 | 0.28 | 4.35 | 14.74 |
| 10-10 | 11.53 | 1.49 | 0.66 | 16.71 | 1.07 | 1.59 | 0.60 | 4.10 | 5.62 | 31.15 | 5.63 | nd | nd | 2.62 | 12.25 |
| 10-11 | 15.42 | 1.63 | 0.56 | 14.45 | 1.63 | 1.88 | 0.71 | 4.08 | 6.08 | 27.34 | 5.37 | nd | nd | 2.08 | 13.75 |
| 10-13 | 13.26 | 1.53 | 0.56 | 12.91 | 2.42 | 1.84 | 0.88 | 4.85 | 5.43 | 30.49 | 4.23 | nd | nd | 3.37 | 13.68 |
| 10-14 | 14.92 | 1.55 | 1.13 | 12.72 | 1.88 | 1.46 | 0.68 | 4.76 | 5.19 | 30.23 | 4.24 | 0.46 | 0.27 | 2.68 | 12.78 |

TABLE 4

Analysis of various plant organs of non-transgenic and transgenic lines (pGPTV-D6D5E6(Tp)ω3Pi). The fatty acids are indicated in percentages.

| Fatty acids (w %) | Seeds WT | Seeds 35S | Leaves WT | Leaves 35S | Stalks WT | Stalks 35S | Flowers WT | Flowers 35S |
|---|---|---|---|---|---|---|---|---|
| 16:3 | — | | 14.34 | 13.59 | 2.31 | 4.18 | 2.35 | 1.76 |
| 18:1 (n9) | 33.22 | 45.43 | 0.93 | 1.97 | 1.54 | 3.84 | 1.26 | 1.51 |
| LA | 45.17 | 30.34 | 11.79 | 4.36 | 21.60 | 15.88 | 14.31 | 13.18 |
| GLA (18:3, d6, 9, 12) | | 0.55 | | 5.45 | | 1.14 | | 0.86 |
| ALA (18:3, d9, 12, 15) | 9.66 | 10.61 | 53.28 | 28.94 | 46.04 | 43.36 | 36.72 | 36.10 |
| SDA (18:4, d6, 9, 12, 15) | | 0.13 | | 4.77 | | 1.52 | | 0.52 |
| ARA (20:4 d5, 8, 11, 14) | | 0.10 | | 0.28 | | | | |
| EPA (20:5, d5, 8, 11, 14, 17) | | 0.10 | | 13.44 | | 0.79 | | 0.72 |

EQUIVALENTS

Many equivalents of the specific embodiments according to the invention described herein can be identified or determined by the skilled worker resorting simply to routine experiments. These equivalents are intended to be within the scope of the claims.

We claim:

1. A process for producing arachidonic acid or eicosapentaenoic acid or arachidonic acid and eicosapentaenoic acid in the vegetative tissue of a transgenic plant with a content of at least 4% by weight based on the total lipid content of the transgenic plant, the process comprising:
   a) introducing at least one nucleic acid sequence coding for a polypeptide having Δ6-desaturase activity into the plant, and
   b) introducing at least one nucleic acid sequence coding for a polypeptide having Δ6-elongase activity into the plant, and
   c) introducing at least one nucleic acid sequence coding for a polypeptide having Δ5-desaturase activity into the plant, and
   wherein the sequences indicated in steps (a) to (c) are expressed with the aid of at least one constitutive CaMV/35S promoter and terminator in the plant;
   wherein said promoter allows for the expression of the sequences indicated in steps (a) to (c) in vegetative tissue of said plant; and
   wherein the nucleic acid sequence coding for a polypeptide having Δ5-desaturase activity is selected from the group consisting of:
   i) a nucleic acid sequence comprising the sequence of SEQ ID NO: 5,
   ii) a nucleic acid sequence encoding a polypeptide comprising the amino acid sequence of SEQ ID NO: 6, and
   iii) a nucleic acid sequence which codes for a polypeptide comprising an amino acid sequence having at least 70% homology at the amino acid level to SEQ ID NO: 6, and has Δ5-desaturase activity.

2. The process according to claim 1, wherein a nucleic acid sequence coding for an ω3-desaturase is additionally introduced into the plant.

3. The process according to claim 2, wherein the nucleic acid sequence coding for a polypeptide having ω3-desaturase activity is selected from the group consisting of:
   i) a nucleic acid sequence comprising the sequence of SEQ ID NO: 9,
   ii) a nucleic acid sequence encoding a polypeptide comprising the amino acid sequence of SEQ ID NO: 10, and
   iii) a nucleic acid sequence which encodes a polypeptide comprising an amino acid sequence having at least 80% homology at the amino acid level to SEQ ID NO: 10 and has ω3-desaturase activity.

4. The process according to claim 1, wherein the arachidonic acid or eicosapentaenoic acid or arachidonic acid and eicosapentaenoic acid are mainly bound in the form of their esters in phospholipids or triacylglycerides in the plant.

5. The process according to claim 4, wherein the arachidonic acid or eicosapentaenoic acid or arachidonic acid and eicosapentaenoic acid are mainly bound in the form of their esters in the phospholipids and wherein the phospholipid esters have an arachidonic acid or eicosapentaenoic acid content of at least 10% by weight based on total lipids.

6. The process according to claim 4, wherein the arachidonic acid or eicosapentaenoic acid or arachidonic acid and eicosapentaenoic acid are mainly bound in the form of their esters in the triacylglycerides and wherein the triacylglyceride esters have an arachidonic acid or eicosapentaenoic acid content of at least 10% by weight based on total lipids.

7. The process according to claim 1, wherein the plant is an oil-producing plant, a vegetable plant, salad plant or ornamental.

8. The process according to claim 7, wherein the plant is selected from the group of plant families consisting of the following families: Aceraceae, Actinidiaceae, Anacardiaceae, Apiaceae, Arecaceae, Asteraceae, Arecaceae, Betulaceae, Boraginaceae, Brassicaceae, Bromeliaceae, Cannabaceae, Cannaceae, Caprifoliaceae, Chenopodiaceae, Convolvulaceae, Cucurbitaceae, Dioscoreaceae, Elaeagnaceae, Ericaceae, Euphorbiaceae, Fabaceae, Fagaceae, Grossulariaceae, Juglandaceae, Lauraceae, Liliaceae, Linaceae, Malvaceae, Moraceae, Musaceae, Oleaceae, Oxalidaceae, Papaveraceae, Poaceae, Polygonaceae, Punicaceae, Rosaceae, Rubiaceae, Rutaceae, Scrophulariaceae, Solanaceae, Sterculiaceae and Valerianaceae.

9. The process according to claim 5, wherein the arachidonic acid or eicosapentaenoic acid or arachidonic acid and eicosapentaenoic acid are isolated in the form of their oils, lipids or free fatty acids from the plant.

10. The process according to claim 1, wherein additional further biosynthesis genes of the fatty acid or lipid metabolism selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferase(s), fatty acid synthase (s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases, and fatty acid elongase(s) are introduced into the plant.

11. The process according to claim 10, wherein the additional biosynthesis gene of the fatty acid or lipid metabolism is selected from the group consisting of Δ4-desaturase, Δ5-desaturase, Δ6-desaturase, Δ8-desaturase, Δ9-desaturase, Δ12-desaturase, Δ6-elongase, and Δ9-elongase.

12. The process according to claim 6, wherein the arachidonic acid or eicosapentaenoic acid or arachidonic acid and eicosapentaenoic acid are isolated in the form of their oils, lipids or free fatty acids from the plant.

13. The process according to claim 2, wherein the nucleic acids are expressed in vegetative tissue.

14. The process according to claim 2, wherein the arachidonic acid or eicosapentaenoic acid or arachidonic acid and eicosapentaenoic acid are mainly bound in the form of their esters in phospholipids or triacylglycerides in the plant.

15. The process according to claim 2, wherein additional further biosynthesis genes of the fatty acid or lipid metabolism selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferase(s), fatty acid synthase (s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases, and fatty acid elongase(s) are introduced into the plant.

16. The process according to claim 15, wherein the additional biosynthesis gene of the fatty acid or lipid metabolism is selected from the group consisting of Δ4-desaturase, Δ5-desaturase, Δ6-desaturase, Δ8-desaturase, Δ9-desaturase, Δ12-desaturase, Δ6-elongase, and Δ9-elongase.

17. The process of claim 1, wherein the nucleic acid sequence encodes a polypeptide comprising an amino acid sequence having at least 95% homology at the amino acid level to SEQ ID NO: 6.

18. The process of claim 1, wherein the nucleic acid sequence comprises the sequence of SEQ ID NO: 5 or comprises a sequence encoding the amino acid sequence of SEQ ID NO: 6.

19. The process of claim 3, wherein the nucleic acid sequence encodes a polypeptide comprising an amino acid sequence having at least 95% homology at the amino acid level to SEQ ID NO: 10.

20. The process of claim 3, wherein the nucleic acid sequence comprises the sequence of SEQ ID NO: 9 or comprises a sequence encoding the amino acid sequence of SEQ ID NO: 10.

* * * * *

SEQUENCE LISTING

<160> NUMBER OF SEQ ID NOS: 12

<210> SEQ ID NO 1
<211> LENGTH: 1380
<212> TYPE: DNA
<213> ORGANISM: Pythium irregulare
<220> FEATURE:
<221> NAME/KEY: CDS
<222> LOCATION: (1)..(1380)
<223> OTHER INFORMATION: Delta-6-Desaturase

<400> SEQUENCE: 1

```
atg gtg gac ctc aag cct gga gtg aag cgc ctg gtg agc tgg aag gag      48
Met Val Asp Leu Lys Pro Gly Val Lys Arg Leu Val Ser Trp Lys Glu
1               5                   10                  15 atc cgc gag cac gcg acg ccc gcg acc gcg tgg atc gtg att cac cac      96
Ile Arg Glu His Ala Thr Pro Ala Thr Ala Trp Ile Val Ile His His
            20                  25                  30 aag gtc tac gac atc tcc aag tgg gac tcg cac ccg ggt ggc tcc gtg     144
Lys Val Tyr Asp Ile Ser Lys Trp Asp Ser His Pro Gly Gly Ser Val
        35                  40                  45 atg ctc acg cag gcc ggc gag gac gcc acg gac gcc ttc gcg gtc ttc     192
Met Leu Thr Gln Ala Gly Glu Asp Ala Thr Asp Ala Phe Ala Val Phe
    50                  55                  60 cac ccg tcc tcg gcg ctc aag ctg ctc gag cag ttc tac gtc ggc gac     240
His Pro Ser Ser Ala Leu Lys Leu Leu Glu Gln Phe Tyr Val Gly Asp
65                  70                  75                  80 gtg gac gaa acc tcc aag gcc gag atc gag ggg gag ccg gcg agc gac     288
Val Asp Glu Thr Ser Lys Ala Glu Ile Glu Gly Glu Pro Ala Ser Asp
                85                  90                  95 gag gag cgc gcg cgc cgc gag cgc atc aac gag ttc atc gcg tcc tac     336
Glu Glu Arg Ala Arg Arg Glu Arg Ile Asn Glu Phe Ile Ala Ser Tyr
            100                 105                 110 cgc cgt ctg cgc gtc aag gtc aag ggc atg ggg ctc tac gac gcc agc     384
Arg Arg Leu Arg Val Lys Val Lys Gly Met Gly Leu Tyr Asp Ala Ser
        115                 120                 125 gcg ctc tac tac gcg tgg aag ctc gtg agc acg ttc ggc atc gcg gtg     432
Ala Leu Tyr Tyr Ala Trp Lys Leu Val Ser Thr Phe Gly Ile Ala Val
    130                 135                 140
```

```
ctc tcg atg gcg atc tgc ttc ttc ttc aac agt ttc gcc atg tac atg      480
Leu Ser Met Ala Ile Cys Phe Phe Phe Asn Ser Phe Ala Met Tyr Met
145                 150                 155                 160 gtc gcc ggc gtg att atg ggg ctc ttc tac cag cag tcc gga tgg ctg      528
Val Ala Gly Val Ile Met Gly Leu Phe Tyr Gln Gln Ser Gly Trp Leu
                165                 170                 175 gcg cac gac ttc ttg cac aac cag gtg tgc gag aac cgc acg ctc ggc      576
Ala His Asp Phe Leu His Asn Gln Val Cys Glu Asn Arg Thr Leu Gly
            180                 185                 190 aac ctt atc ggc tgc ctc gtg ggc aac gcc tgg cag ggc ttc agc atg      624
Asn Leu Ile Gly Cys Leu Val Gly Asn Ala Trp Gln Gly Phe Ser Met
        195                 200                 205 cag tgg tgg aag aac aag cac aac ctg cac cac gcg gtg ccg aac ctg      672
Gln Trp Trp Lys Asn Lys His Asn Leu His His Ala Val Pro Asn Leu
    210                 215                 220 cac agc gcc aag gac gag ggc ttc atc ggc gac ccg gac atc gac acc      720
His Ser Ala Lys Asp Glu Gly Phe Ile Gly Asp Pro Asp Ile Asp Thr
225                 230                 235                 240 atg ccg ctg ctg gcg tgg tct aag gag atg gcg cgc aag gcg ttc gag      768
Met Pro Leu Leu Ala Trp Ser Lys Glu Met Ala Arg Lys Ala Phe Glu
                245                 250                 255 tcg gcg cac ggc ccg ttc ttc atc cgc aac cag gcg ttc cta tac ttc      816
Ser Ala His Gly Pro Phe Phe Ile Arg Asn Gln Ala Phe Leu Tyr Phe
            260                 265                 270 ccg ctg ctg ctg ctc gcg cgc ctg agc tgg ctc gcg cag tcg ttc ttc      864
Pro Leu Leu Leu Leu Ala Arg Leu Ser Trp Leu Ala Gln Ser Phe Phe
        275                 280                 285 tac gtg ttc acc gag ttc tcg ttc ggc atc ttc gac aag gtc gag ttc      912
Tyr Val Phe Thr Glu Phe Ser Phe Gly Ile Phe Asp Lys Val Glu Phe
    290                 295                 300 gac gga ccg gag aag gcg ggt ctg atc gtg cac tac atc tgg cag ctc      960
Asp Gly Pro Glu Lys Ala Gly Leu Ile Val His Tyr Ile Trp Gln Leu
305                 310                 315                 320 gcg atc ccg tac ttc tgc aac atg agc ctg ttt gag ggc gtg gca tac     1008
Ala Ile Pro Tyr Phe Cys Asn Met Ser Leu Phe Glu Gly Val Ala Tyr
                325                 330                 335 ttc ctc atg ggc cag gcg tcc tgc ggc ttg ctc ctg gcg ctg gtg ttc     1056
Phe Leu Met Gly Gln Ala Ser Cys Gly Leu Leu Leu Ala Leu Val Phe
            340                 345                 350 agt att ggc cac aac ggc atg tcg gtg tac gag cgc gaa acc aag ccg     1104
Ser Ile Gly His Asn Gly Met Ser Val Tyr Glu Arg Glu Thr Lys Pro
        355                 360                 365 gac ttc tgg cag ctg cag gtg acc acg acg cgc aac atc cgc gcg tcg     1152
Asp Phe Trp Gln Leu Gln Val Thr Thr Thr Arg Asn Ile Arg Ala Ser
    370                 375                 380 gta ttc atg gac tgg ttc acc ggt ggc ttg aac tac cag atc gac cat     1200
Val Phe Met Asp Trp Phe Thr Gly Gly Leu Asn Tyr Gln Ile Asp His
385                 390                 395                 400 cac ctg ttc ccg ctc gtg ccg cgc cac aac ttg cca aag gtc aac gtg     1248
His Leu Phe Pro Leu Val Pro Arg His Asn Leu Pro Lys Val Asn Val
                405                 410                 415 ctc atc aag tcg cta tgc aag gag ttc gac atc ccg ttc cac gag acc     1296
Leu Ile Lys Ser Leu Cys Lys Glu Phe Asp Ile Pro Phe His Glu Thr
            420                 425                 430 ggc ttc tgg gag ggc atc tac gag gtc gtg gac cac ctg gcg gac atc     1344
Gly Phe Trp Glu Gly Ile Tyr Glu Val Val Asp His Leu Ala Asp Ile
        435                 440                 445 agc aag gaa ttt atc acc gag ttc cca gcg atg taa                     1380
Ser Lys Glu Phe Ile Thr Glu Phe Pro Ala Met
    450                 455
```

```
<210> SEQ ID NO 2
<211> LENGTH: 459
<212> TYPE: PRT
<213> ORGANISM: Pythium irregulare

<400> SEQUENCE: 2

Met Val Asp Leu Lys Pro Gly Val Lys Arg Leu Val Ser Trp Lys Glu
 1               5                   10                  15

Ile Arg Glu His Ala Thr Pro Ala Thr Ala Trp Ile Val Ile His His
                20                  25                  30

Lys Val Tyr Asp Ile Ser Lys Trp Asp Ser His Pro Gly Gly Ser Val
            35                  40                  45

Met Leu Thr Gln Ala Gly Glu Asp Ala Thr Asp Ala Phe Ala Val Phe
50                  55                  60

His Pro Ser Ser Ala Leu Lys Leu Leu Glu Gln Phe Tyr Val Gly Asp
65                  70                  75                  80

Val Asp Glu Thr Ser Lys Ala Glu Ile Glu Gly Glu Pro Ala Ser Asp
                85                  90                  95

Glu Glu Arg Ala Arg Arg Glu Arg Ile Asn Glu Phe Ile Ala Ser Tyr
            100                 105                 110

Arg Arg Leu Arg Val Lys Val Lys Gly Met Gly Leu Tyr Asp Ala Ser
        115                 120                 125

Ala Leu Tyr Tyr Ala Trp Lys Leu Val Ser Thr Phe Gly Ile Ala Val
130                 135                 140

Leu Ser Met Ala Ile Cys Phe Phe Asn Ser Phe Ala Met Tyr Met
145                 150                 155                 160

Val Ala Gly Val Ile Met Gly Leu Phe Tyr Gln Gln Ser Gly Trp Leu
                165                 170                 175

Ala His Asp Phe Leu His Asn Gln Val Cys Glu Asn Arg Thr Leu Gly
            180                 185                 190

Asn Leu Ile Gly Cys Leu Val Gly Asn Ala Trp Gln Gly Phe Ser Met
        195                 200                 205

Gln Trp Trp Lys Asn Lys His Asn Leu His His Ala Val Pro Asn Leu
210                 215                 220

His Ser Ala Lys Asp Glu Gly Phe Ile Gly Asp Pro Asp Ile Asp Thr
225                 230                 235                 240

Met Pro Leu Leu Ala Trp Ser Lys Glu Met Ala Arg Lys Ala Phe Glu
                245                 250                 255

Ser Ala His Gly Pro Phe Phe Ile Arg Asn Gln Ala Phe Leu Tyr Phe
            260                 265                 270

Pro Leu Leu Leu Leu Ala Arg Leu Ser Trp Leu Ala Gln Ser Phe Phe
        275                 280                 285

Tyr Val Phe Thr Glu Phe Ser Phe Gly Ile Phe Asp Lys Val Glu Phe
290                 295                 300

Asp Gly Pro Glu Lys Ala Gly Leu Ile Val His Tyr Ile Trp Gln Leu
305                 310                 315                 320

Ala Ile Pro Tyr Phe Cys Asn Met Ser Leu Phe Glu Gly Val Ala Tyr
                325                 330                 335

Phe Leu Met Gly Gln Ala Ser Cys Gly Leu Leu Leu Ala Leu Val Phe
            340                 345                 350

Ser Ile Gly His Asn Gly Met Ser Val Tyr Glu Arg Glu Thr Lys Pro
        355                 360                 365

Asp Phe Trp Gln Leu Gln Val Thr Thr Thr Arg Asn Ile Arg Ala Ser
370                 375                 380
```

-continued

```
Val Phe Met Asp Trp Phe Thr Gly Gly Leu Asn Tyr Gln Ile Asp His
385                 390                 395                 400

His Leu Phe Pro Leu Val Pro Arg His Asn Leu Pro Lys Val Asn Val
            405                 410                 415

Leu Ile Lys Ser Leu Cys Lys Glu Phe Asp Ile Pro Phe His Glu Thr
        420                 425                 430

Gly Phe Trp Glu Gly Ile Tyr Glu Val Val Asp His Leu Ala Asp Ile
    435                 440                 445

Ser Lys Glu Phe Ile Thr Glu Phe Pro Ala Met
    450                 455
```

<210> SEQ ID NO 3
<211> LENGTH: 831
<212> TYPE: DNA
<213> ORGANISM: Traustochytrium sp.
<220> FEATURE:
<221> NAME/KEY: CDS
<222> LOCATION: (1)..(831)
<223> OTHER INFORMATION: Delta-6-Elongase

<400> SEQUENCE: 3

```
atg gac gtc gtc gag cag caa tgg cgc cgc ttc gtg gac gcc gtg gac      48
Met Asp Val Val Glu Gln Gln Trp Arg Arg Phe Val Asp Ala Val Asp
1               5                   10                  15 aac gga atc gtg gag ttc atg gag cat gag aag ccc aac aag ctg aac      96
Asn Gly Ile Val Glu Phe Met Glu His Glu Lys Pro Asn Lys Leu Asn
            20                  25                  30 gag ggc aag ctc ttc acc tcg acc gag gag atg atg gcg ctt atc gtc     144
Glu Gly Lys Leu Phe Thr Ser Thr Glu Glu Met Met Ala Leu Ile Val
        35                  40                  45 ggc tac ctg gcg ttc gtg gtc ctc ggg tcc gcc ttc atg aag gcc ttt     192
Gly Tyr Leu Ala Phe Val Val Leu Gly Ser Ala Phe Met Lys Ala Phe
    50                  55                  60 gtc gat aag cct ttc gag ctc aag ttc ctc aag ctc gtg cac aac atc     240
Val Asp Lys Pro Phe Glu Leu Lys Phe Leu Lys Leu Val His Asn Ile
65                  70                  75                  80 ttc ctc acc ggt ctg tcc atg tac atg gcc acc gag tgc gcg cgc cag     288
Phe Leu Thr Gly Leu Ser Met Tyr Met Ala Thr Glu Cys Ala Arg Gln
                85                  90                  95 gca tac ctc ggc ggc tac aag ctc ttt ggc aac ccg atg gag aag ggc     336
Ala Tyr Leu Gly Gly Tyr Lys Leu Phe Gly Asn Pro Met Glu Lys Gly
            100                 105                 110 acc gag tcg cac gcc ccg ggc atg gcc aac atc atc tac atc ttc tac     384
Thr Glu Ser His Ala Pro Gly Met Ala Asn Ile Ile Tyr Ile Phe Tyr
        115                 120                 125 gtg agc aag ttc ctc gaa ttc ctc gac acc gtc ttc atg atc ctc ggc     432
Val Ser Lys Phe Leu Glu Phe Leu Asp Thr Val Phe Met Ile Leu Gly
    130                 135                 140 aag aag tgg aag cag ctc agc ttt ctc cac gtc tac cac cac gcg agc     480
Lys Lys Trp Lys Gln Leu Ser Phe Leu His Val Tyr His His Ala Ser
145                 150                 155                 160 atc agc ttc atc tgg ggc atc atc gcc cgc ttc gcg ccc ggt ggc gac     528
Ile Ser Phe Ile Trp Gly Ile Ile Ala Arg Phe Ala Pro Gly Gly Asp
                165                 170                 175 gcc tac ttc tct acc atc ctc aac agc agc gtg cat gtc gtg ctc tac     576
Ala Tyr Phe Ser Thr Ile Leu Asn Ser Ser Val His Val Val Leu Tyr
            180                 185                 190 ggc tac tac gcc tcg acc acc ctc ggc tac acc ttc atg cgc ccg ctg     624
Gly Tyr Tyr Ala Ser Thr Thr Leu Gly Tyr Thr Phe Met Arg Pro Leu
        195                 200                 205 cgc ccg tac att acc acc att cag ctc acg cag ttc atg gcc atg gtc     672
```

```
Arg Pro Tyr Ile Thr Thr Ile Gln Leu Thr Gln Phe Met Ala Met Val
    210                 215                 220 gtc cag tcc gtc tat gac tac tac aac ccc tgc gac tac ccg cag ccc      720
Val Gln Ser Val Tyr Asp Tyr Tyr Asn Pro Cys Asp Tyr Pro Gln Pro
225                 230                 235                 240 ctc gtc aag ctg ctc ttc tgg tac atg ctc acc atg ctc ggc ctc ttc      768
Leu Val Lys Leu Leu Phe Trp Tyr Met Leu Thr Met Leu Gly Leu Phe
                245                 250                 255 ggc aac ttc ttc gtg cag cag tac ctc aag ccc aag gcg ccc aag aag      816
Gly Asn Phe Phe Val Gln Gln Tyr Leu Lys Pro Lys Ala Pro Lys Lys
            260                 265                 270 cag aag acc atc taa                                                  831
Gln Lys Thr Ile
        275
```

<210> SEQ ID NO 4
<211> LENGTH: 276
<212> TYPE: PRT
<213> ORGANISM: Traustochytrium sp.

<400> SEQUENCE: 4

```
Met Asp Val Val Glu Gln Gln Trp Arg Arg Phe Val Asp Ala Val Asp
1               5                   10                  15

Asn Gly Ile Val Glu Phe Met Glu His Glu Lys Pro Asn Lys Leu Asn
                20                  25                  30

Glu Gly Lys Leu Phe Thr Ser Thr Glu Glu Met Met Ala Leu Ile Val
            35                  40                  45

Gly Tyr Leu Ala Phe Val Val Leu Gly Ser Ala Phe Met Lys Ala Phe
    50                  55                  60

Val Asp Lys Pro Phe Glu Leu Lys Phe Lys Leu Val His Asn Ile
65                  70                  75                  80

Phe Leu Thr Gly Leu Ser Met Tyr Met Ala Thr Glu Cys Ala Arg Gln
                85                  90                  95

Ala Tyr Leu Gly Gly Tyr Lys Leu Phe Gly Asn Pro Met Glu Lys Gly
            100                 105                 110

Thr Glu Ser His Ala Pro Gly Met Ala Asn Ile Ile Tyr Ile Phe Tyr
        115                 120                 125

Val Ser Lys Phe Leu Glu Phe Leu Asp Thr Val Phe Met Ile Leu Gly
    130                 135                 140

Lys Lys Trp Lys Gln Leu Ser Phe Leu His Val Tyr His His Ala Ser
145                 150                 155                 160

Ile Ser Phe Ile Trp Gly Ile Ile Ala Arg Phe Ala Pro Gly Gly Asp
                165                 170                 175

Ala Tyr Phe Ser Thr Ile Leu Asn Ser Ser Val His Val Leu Tyr
            180                 185                 190

Gly Tyr Tyr Ala Ser Thr Thr Leu Gly Tyr Thr Phe Met Arg Pro Leu
        195                 200                 205

Arg Pro Tyr Ile Thr Thr Ile Gln Leu Thr Gln Phe Met Ala Met Val
    210                 215                 220

Val Gln Ser Val Tyr Asp Tyr Tyr Asn Pro Cys Asp Tyr Pro Gln Pro
225                 230                 235                 240

Leu Val Lys Leu Leu Phe Trp Tyr Met Leu Thr Met Leu Gly Leu Phe
                245                 250                 255

Gly Asn Phe Phe Val Gln Gln Tyr Leu Lys Pro Lys Ala Pro Lys Lys
            260                 265                 270

Gln Lys Thr Ile
        275
```

-continued

<210> SEQ ID NO 5
<211> LENGTH: 1320
<212> TYPE: DNA
<213> ORGANISM: Traustochytrium sp.
<220> FEATURE:
<221> NAME/KEY: CDS
<222> LOCATION: (1)..(1320)
<223> OTHER INFORMATION: Delta-5-Desaturase

<400> SEQUENCE: 5

| | | | | | | | | | | | | | | | | |
|---|---|---|---|---|---|---|---|---|---|---|---|---|---|---|---|---|
| atg | ggc | aag | ggc | agc | gag | ggc | cgc | agc | gcg | gcg | cgc | gag | atg | acg | gcc | 48 |
| Met | Gly | Lys | Gly | Ser | Glu | Gly | Arg | Ser | Ala | Ala | Arg | Glu | Met | Thr | Ala | |
| 1 | | | | 5 | | | | | 10 | | | | | 15 | | |

| gag | gcg | aac | ggc | gac | aag | cgg | aaa | acg | att | ctg | atc | gag | ggc | gtc | ctg | 96 |
|---|---|---|---|---|---|---|---|---|---|---|---|---|---|---|---|---|
| Glu | Ala | Asn | Gly | Asp | Lys | Arg | Lys | Thr | Ile | Leu | Ile | Glu | Gly | Val | Leu | |
| | | | 20 | | | | | 25 | | | | | 30 | | | |

| tac | gac | gcg | acg | aac | ttt | aag | cac | ccg | ggc | ggt | tcg | atc | atc | aac | ttc | 144 |
|---|---|---|---|---|---|---|---|---|---|---|---|---|---|---|---|---|
| Tyr | Asp | Ala | Thr | Asn | Phe | Lys | His | Pro | Gly | Gly | Ser | Ile | Ile | Asn | Phe | |
| | | 35 | | | | | 40 | | | | | 45 | | | | |

| ttg | acc | gag | ggc | gag | gcc | ggc | gtg | gac | gcg | acg | cag | gcg | tac | cgc | gag | 192 |
|---|---|---|---|---|---|---|---|---|---|---|---|---|---|---|---|---|
| Leu | Thr | Glu | Gly | Glu | Ala | Gly | Val | Asp | Ala | Thr | Gln | Ala | Tyr | Arg | Glu | |
| 50 | | | | | 55 | | | | | 60 | | | | | | |

| ttt | cat | cag | cgg | tcc | ggc | aag | gcc | gac | aag | tac | ctc | aag | tcg | ctg | ccg | 240 |
|---|---|---|---|---|---|---|---|---|---|---|---|---|---|---|---|---|
| Phe | His | Gln | Arg | Ser | Gly | Lys | Ala | Asp | Lys | Tyr | Leu | Lys | Ser | Leu | Pro | |
| 65 | | | | | 70 | | | | | 75 | | | | | 80 | |

| aag | ctg | gat | gcg | tcc | aag | gtg | gag | tcg | cgg | ttc | tcg | gcc | aaa | gag | cag | 288 |
|---|---|---|---|---|---|---|---|---|---|---|---|---|---|---|---|---|
| Lys | Leu | Asp | Ala | Ser | Lys | Val | Glu | Ser | Arg | Phe | Ser | Ala | Lys | Glu | Gln | |
| | | | | 85 | | | | | 90 | | | | | 95 | | |

| gcg | cgg | cgc | gac | gcc | atg | acg | cgc | gac | tac | gcg | gcc | ttt | cgc | gag | gag | 336 |
|---|---|---|---|---|---|---|---|---|---|---|---|---|---|---|---|---|
| Ala | Arg | Arg | Asp | Ala | Met | Thr | Arg | Asp | Tyr | Ala | Ala | Phe | Arg | Glu | Glu | |
| | | | 100 | | | | | 105 | | | | | 110 | | | |

| ctc | gtc | gcc | gag | ggg | tac | ttt | gac | ccg | tcg | atc | ccg | cac | atg | att | tac | 384 |
|---|---|---|---|---|---|---|---|---|---|---|---|---|---|---|---|---|
| Leu | Val | Ala | Glu | Gly | Tyr | Phe | Asp | Pro | Ser | Ile | Pro | His | Met | Ile | Tyr | |
| | | 115 | | | | | 120 | | | | | 125 | | | | |

| cgc | gtc | gtg | gag | atc | gtg | gcg | ctc | ttc | gcg | ctc | tcg | ttc | tgg | ctc | atg | 432 |
|---|---|---|---|---|---|---|---|---|---|---|---|---|---|---|---|---|
| Arg | Val | Val | Glu | Ile | Val | Ala | Leu | Phe | Ala | Leu | Ser | Phe | Trp | Leu | Met | |
| | 130 | | | | | 135 | | | | | 140 | | | | | |

| tcc | aag | gcc | tcg | ccc | acc | tcg | ctc | gtg | ctg | ggc | gtg | gtg | atg | aac | ggc | 480 |
|---|---|---|---|---|---|---|---|---|---|---|---|---|---|---|---|---|
| Ser | Lys | Ala | Ser | Pro | Thr | Ser | Leu | Val | Leu | Gly | Val | Val | Met | Asn | Gly | |
| 145 | | | | | 150 | | | | | 155 | | | | | 160 | |

| att | gcg | cag | ggc | cgc | tgc | ggc | tgg | gtc | atg | cac | gag | atg | ggc | cac | ggg | 528 |
|---|---|---|---|---|---|---|---|---|---|---|---|---|---|---|---|---|
| Ile | Ala | Gln | Gly | Arg | Cys | Gly | Trp | Val | Met | His | Glu | Met | Gly | His | Gly | |
| | | | | 165 | | | | | 170 | | | | | 175 | | |

| tcg | ttc | acg | ggc | gtc | atc | tgg | ctc | gac | gac | cgg | atg | tgc | gag | ttc | ttc | 576 |
|---|---|---|---|---|---|---|---|---|---|---|---|---|---|---|---|---|
| Ser | Phe | Thr | Gly | Val | Ile | Trp | Leu | Asp | Asp | Arg | Met | Cys | Glu | Phe | Phe | |
| | | | 180 | | | | | 185 | | | | | 190 | | | |

| tac | ggc | gtc | ggc | tgc | ggc | atg | agc | ggg | cac | tac | tgg | aag | aac | cag | cac | 624 |
|---|---|---|---|---|---|---|---|---|---|---|---|---|---|---|---|---|
| Tyr | Gly | Val | Gly | Cys | Gly | Met | Ser | Gly | His | Tyr | Trp | Lys | Asn | Gln | His | |
| | | 195 | | | | | 200 | | | | | 205 | | | | |

| agc | aag | cac | cac | gcc | gcg | ccc | aac | cgc | ctc | gag | cac | gat | gtc | gat | ctc | 672 |
|---|---|---|---|---|---|---|---|---|---|---|---|---|---|---|---|---|
| Ser | Lys | His | His | Ala | Ala | Pro | Asn | Arg | Leu | Glu | His | Asp | Val | Asp | Leu | |
| | 210 | | | | | 215 | | | | | 220 | | | | | |

| aac | acg | ctg | ccc | ctg | gtc | gcc | ttt | aac | gag | cgc | gtc | gtg | cgc | aag | gtc | 720 |
|---|---|---|---|---|---|---|---|---|---|---|---|---|---|---|---|---|
| Asn | Thr | Leu | Pro | Leu | Val | Ala | Phe | Asn | Glu | Arg | Val | Val | Arg | Lys | Val | |
| 225 | | | | | 230 | | | | | 235 | | | | | 240 | |

| aag | ccg | gga | tcg | ctg | ctg | gcg | ctc | tgg | ctg | cgc | gtg | cag | gcg | tac | ctc | 768 |
|---|---|---|---|---|---|---|---|---|---|---|---|---|---|---|---|---|
| Lys | Pro | Gly | Ser | Leu | Leu | Ala | Leu | Trp | Leu | Arg | Val | Gln | Ala | Tyr | Leu | |
| | | | | 245 | | | | | 250 | | | | | 255 | | |

| ttt | gcg | ccc | gtc | tcg | tgc | ctg | ctc | atc | ggc | ctt | ggc | tgg | acg | ctc | tac | 816 |
|---|---|---|---|---|---|---|---|---|---|---|---|---|---|---|---|---|
| Phe | Ala | Pro | Val | Ser | Cys | Leu | Leu | Ile | Gly | Leu | Gly | Trp | Thr | Leu | Tyr | |
| | | | 260 | | | | | 265 | | | | | 270 | | | |

-continued

| | | |
|---|---|---|
| ctg cac ccg cgc tac atg ctg cgc acc aag cgg cac atg gag ttc gtc<br>Leu His Pro Arg Tyr Met Leu Arg Thr Lys Arg His Met Glu Phe Val<br>     275                    280                     285 | 864 |
| tgg atc ttc gcg cgc tac att ggc tgg ttc tcg ctc atg ggc gct ctc<br>Trp Ile Phe Ala Arg Tyr Ile Gly Trp Phe Ser Leu Met Gly Ala Leu<br>290                      295                     300 | 912 |
| ggc tac tcg ccg ggc acc tcg gtc ggg atg tac ctg tgc tcg ttc ggc<br>Gly Tyr Ser Pro Gly Thr Ser Val Gly Met Tyr Leu Cys Ser Phe Gly<br>305                      310                     315               320 | 960 |
| ctc ggc tgc att tac att ttc ctg cag ttc gcc gtc agc cac acg cac<br>Leu Gly Cys Ile Tyr Ile Phe Leu Gln Phe Ala Val Ser His Thr His<br>                  325                     330                     335 | 1008 |
| ctg ccg gtg acc aac ccg gag gac cag ctg cac tgg ctc gag tac gcg<br>Leu Pro Val Thr Asn Pro Glu Asp Gln Leu His Trp Leu Glu Tyr Ala<br>                      340                     345                     350 | 1056 |
| gcc gac cac acg gtg aac att agc acc aag tcc tgg ctc gtc acg tgg<br>Ala Asp His Thr Val Asn Ile Ser Thr Lys Ser Trp Leu Val Thr Trp<br>                  355                     360                     365 | 1104 |
| tgg atg tcg aac ctg aac ttt cag atc gag cac cac ctc ttc ccc acg<br>Trp Met Ser Asn Leu Asn Phe Gln Ile Glu His His Leu Phe Pro Thr<br>370                      375                     380 | 1152 |
| gcg ccg cag ttc cgc ttc aag gaa atc agt cct cgc gtc gag gcc ctc<br>Ala Pro Gln Phe Arg Phe Lys Glu Ile Ser Pro Arg Val Glu Ala Leu<br>385                      390                     395               400 | 1200 |
| ttc aag cgc cac aac ctc ccg tac tac gac ctg ccc tac acg agc gcg<br>Phe Lys Arg His Asn Leu Pro Tyr Tyr Asp Leu Pro Tyr Thr Ser Ala<br>                  405                     410                     415 | 1248 |
| gtc tcg acc acc ttt gcc aat ctt tat tcc gtc ggc cac tcg gtc ggc<br>Val Ser Thr Thr Phe Ala Asn Leu Tyr Ser Val Gly His Ser Val Gly<br>                    420                     425                     430 | 1296 |
| gcc gac acc aag aag cag gac tga<br>Ala Asp Thr Lys Lys Gln Asp<br>                  435 | 1320 |

<210> SEQ ID NO 6
<211> LENGTH: 439
<212> TYPE: PRT
<213> ORGANISM: Traustochytrium sp.

<400> SEQUENCE: 6

Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

```
Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
        435

<210> SEQ ID NO 7
<211> LENGTH: 819
<212> TYPE: DNA
<213> ORGANISM: Talassiosira pseudonana
<220> FEATURE:
<221> NAME/KEY: CDS
<222> LOCATION: (1)..(819)
<223> OTHER INFORMATION: Delta-6-Elongase

<400> SEQUENCE: 7 atg gac gcc tac aac gct gca atg gat aag atc ggt gcc gcc atc atc      48
Met Asp Ala Tyr Asn Ala Ala Met Asp Lys Ile Gly Ala Ala Ile Ile
1               5                   10                  15 gat tgg tct gat ccc gat gga aag ttc cgt gcc gat aga gag gac tgg      96
Asp Trp Ser Asp Pro Asp Gly Lys Phe Arg Ala Asp Arg Glu Asp Trp
            20                  25                  30 tgg ctc tgc gac ttc cgt agc gcc atc acc atc gcc ctc atc tac atc     144
Trp Leu Cys Asp Phe Arg Ser Ala Ile Thr Ile Ala Leu Ile Tyr Ile
        35                  40                  45
```

```
gcc ttc gtc atc ctc ggt tcc gcc gtc atg caa tcc ctc ccc gca atg      192
Ala Phe Val Ile Leu Gly Ser Ala Val Met Gln Ser Leu Pro Ala Met
         50                  55                  60 gat ccc tac ccc atc aaa ttc ctc tac aac gtc tcc caa atc ttc ctt      240
Asp Pro Tyr Pro Ile Lys Phe Leu Tyr Asn Val Ser Gln Ile Phe Leu
 65                  70                  75                  80 tgt gcc tac atg act gtc gag gcg gga ttt ttg gcc tac cgc aat gga      288
Cys Ala Tyr Met Thr Val Glu Ala Gly Phe Leu Ala Tyr Arg Asn Gly
                 85                  90                  95 tat acc gtc atg cct tgc aat cat ttc aat gtg aat gat cct ccc gtg      336
Tyr Thr Val Met Pro Cys Asn His Phe Asn Val Asn Asp Pro Pro Val
            100                 105                 110 gcg aat ctt ctt tgg ttg ttt tat att tcc aag gtg tgg gac ttt tgg      384
Ala Asn Leu Leu Trp Leu Phe Tyr Ile Ser Lys Val Trp Asp Phe Trp
        115                 120                 125 gat acc att ttc att gtg ttg ggg aag aag tgg cgt caa tta tct ttc      432
Asp Thr Ile Phe Ile Val Leu Gly Lys Lys Trp Arg Gln Leu Ser Phe
130                 135                 140 ttg cat gta tac cat cac acc acc atc ttt cta ttc tat tgg ctg aat      480
Leu His Val Tyr His His Thr Thr Ile Phe Leu Phe Tyr Trp Leu Asn
145                 150                 155                 160 gcc aat gtc ttg tac gat ggt gac atc ttc ctt acc atc ttg ctc aat      528
Ala Asn Val Leu Tyr Asp Gly Asp Ile Phe Leu Thr Ile Leu Leu Asn
                165                 170                 175 gga ttc atc cac acg gtg atg tac acg tat tac ttc atc tgt atg cat      576
Gly Phe Ile His Thr Val Met Tyr Thr Tyr Tyr Phe Ile Cys Met His
            180                 185                 190 acc aaa gat tcc aag acg ggc aag agt ctt cct ata tgg tgg aag tcg      624
Thr Lys Asp Ser Lys Thr Gly Lys Ser Leu Pro Ile Trp Trp Lys Ser
        195                 200                 205 agt ttg acg gcg ttt cag ttg ttg caa ttc act atc atg atg agt cag      672
Ser Leu Thr Ala Phe Gln Leu Leu Gln Phe Thr Ile Met Met Ser Gln
210                 215                 220 gct acc tac ctt gtc ttc cac ggg tgt gat aag gtg tcg ctt cgt atc      720
Ala Thr Tyr Leu Val Phe His Gly Cys Asp Lys Val Ser Leu Arg Ile
225                 230                 235                 240 acg att gtg tac ttt gtg tcc ctt ttg agt ttg ttc ttc ctt ttt gct      768
Thr Ile Val Tyr Phe Val Ser Leu Leu Ser Leu Phe Phe Leu Phe Ala
                245                 250                 255 cag ttc ttt gtg caa tca tac atg gca ccc aaa aag aag aag agt gct      816
Gln Phe Phe Val Gln Ser Tyr Met Ala Pro Lys Lys Lys Lys Ser Ala
            260                 265                 270 tag                                                                  819
```

<210> SEQ ID NO 8
<211> LENGTH: 272
<212> TYPE: PRT
<213> ORGANISM: Talassiosira pseudonana

<400> SEQUENCE: 8

```
Met Asp Ala Tyr Asn Ala Ala Met Asp Lys Ile Gly Ala Ala Ile Ile
 1               5                  10                  15

Asp Trp Ser Asp Pro Asp Gly Lys Phe Arg Ala Asp Arg Glu Asp Trp
             20                  25                  30

Trp Leu Cys Asp Phe Arg Ser Ala Ile Thr Ile Ala Leu Ile Tyr Ile
         35                  40                  45

Ala Phe Val Ile Leu Gly Ser Ala Val Met Gln Ser Leu Pro Ala Met
     50                  55                  60

Asp Pro Tyr Pro Ile Lys Phe Leu Tyr Asn Val Ser Gln Ile Phe Leu
```

```
            65                  70                  75                  80
Cys Ala Tyr Met Thr Val Glu Ala Gly Phe Leu Ala Tyr Arg Asn Gly
                85                  90                  95

Tyr Thr Val Met Pro Cys Asn His Phe Asn Val Asn Asp Pro Pro Val
            100                 105                 110

Ala Asn Leu Leu Trp Leu Phe Tyr Ile Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Ser Leu Leu Ser Leu Phe Phe Leu Phe Ala
                245                 250                 255

Gln Phe Phe Val Gln Ser Tyr Met Ala Pro Lys Lys Lys Lys Ser Ala
            260                 265                 270

<210> SEQ ID NO 9
<211> LENGTH: 1086
<212> TYPE: DNA
<213> ORGANISM: Phytophthora infestans
<220> FEATURE:
<221> NAME/KEY: CDS
<222> LOCATION: (1)..(1086)
<223> OTHER INFORMATION: Omega-3-Desaturase

<400> SEQUENCE: 9 atg gcg acg aag gag gcg tat gtg ttc ccc act ctg acg gag atc aag      48
Met Ala Thr Lys Glu Ala Tyr Val Phe Pro Thr Leu Thr Glu Ile Lys
1               5                   10                  15 cgg tcg cta cct aaa gac tgt ttc gag gct tcg gtg cct ctg tcg ctc      96
Arg Ser Leu Pro Lys Asp Cys Phe Glu Ala Ser Val Pro Leu Ser Leu
            20                  25                  30 tac tac acc gtg cgt tgt ctg gtg atc gcg gtg gct cta acc ttc ggt     144
Tyr Tyr Thr Val Arg Cys Leu Val Ile Ala Val Ala Leu Thr Phe Gly
        35                  40                  45 ctc aac tac gct cgc gct ctg ccc gag gtc gag agc ttc tgg gct ctg     192
Leu Asn Tyr Ala Arg Ala Leu Pro Glu Val Glu Ser Phe Trp Ala Leu
    50                  55                  60 gac gcc gca ctc tgc acg ggc tac atc ttg ctg cag ggc atc gtg ttc     240
Asp Ala Ala Leu Cys Thr Gly Tyr Ile Leu Leu Gln Gly Ile Val Phe
65                  70                  75                  80 tgg ggc ttc ttc acg gtg ggc cac gat gcc ggc cac ggc gcc ttc tcg     288
Trp Gly Phe Phe Thr Val Gly His Asp Ala Gly His Gly Ala Phe Ser
                85                  90                  95 cgc tac cac ctg ctt aac ttc gtg gtg ggc act ttc atg cac tcg ctc     336
Arg Tyr His Leu Leu Asn Phe Val Val Gly Thr Phe Met His Ser Leu
            100                 105                 110 atc ctc acg ccc ttc gag tcg tgg aag ctc acg cac cgt cac cac cac     384
Ile Leu Thr Pro Phe Glu Ser Trp Lys Leu Thr His Arg His His His
```

```
                    115                 120                 125
aag aac acg ggc aac att gac cgt gac gag gtc ttc tac ccg caa cgc     432
Lys Asn Thr Gly Asn Ile Asp Arg Asp Glu Val Phe Tyr Pro Gln Arg
        130                 135                 140 aag gcc gac gac cac ccg ctg tct cgc aac ctg att ctg gcc ctc ggg     480
Lys Ala Asp Asp His Pro Leu Ser Arg Asn Leu Ile Leu Ala Leu Gly
145                 150                 155                 160 gca gcg tgg ctc gcc tat ttg gtc gag ggc ttc cct cct cgt aag gtc     528
Ala Ala Trp Leu Ala Tyr Leu Val Glu Gly Phe Pro Pro Arg Lys Val
                165                 170                 175 aac cac ttc aac ccg ttc gag cct ctg ttc gtg cgt cag gtg tca gct     576
Asn His Phe Asn Pro Phe Glu Pro Leu Phe Val Arg Gln Val Ser Ala
        180                 185                 190 gtg gta atc tct ctt ctc gcc cac ttc ttc gtg gcc gga ctc tcc atc     624
Val Val Ile Ser Leu Leu Ala His Phe Phe Val Ala Gly Leu Ser Ile
                195                 200                 205 tat ctg agc ctc cag ctg ggc ctt aag acg atg gca atc tac tac tat     672
Tyr Leu Ser Leu Gln Leu Gly Leu Lys Thr Met Ala Ile Tyr Tyr Tyr
        210                 215                 220 gga cct gtt ttt gtg ttc ggc agc atg ctg gtc att acc acc ttc cta     720
Gly Pro Val Phe Val Phe Gly Ser Met Leu Val Ile Thr Thr Phe Leu
225                 230                 235                 240 cac cac aat gat gag gag acc cca tgg tac gcc gac tcg gag tgg acg     768
His His Asn Asp Glu Glu Thr Pro Trp Tyr Ala Asp Ser Glu Trp Thr
                245                 250                 255 tac gtc aag ggc aac ctc tcg tcc gtg gac cga tcg tac ggc gcg ctc     816
Tyr Val Lys Gly Asn Leu Ser Ser Val Asp Arg Ser Tyr Gly Ala Leu
        260                 265                 270 att gac aac ctg agc cac aac atc ggc acg cac cag atc cac cac ctt     864
Ile Asp Asn Leu Ser His Asn Ile Gly Thr His Gln Ile His His Leu
                275                 280                 285 ttc cct atc att ccg cac tac aaa ctc aag aaa gcc act gcg gcc ttc     912
Phe Pro Ile Ile Pro His Tyr Lys Leu Lys Lys Ala Thr Ala Ala Phe
        290                 295                 300 cac cag gct ttc cct gag ctc gtg cgc aag agc gac gag cca att atc     960
His Gln Ala Phe Pro Glu Leu Val Arg Lys Ser Asp Glu Pro Ile Ile
305                 310                 315                 320 aag gct ttc ttc cgg gtt gga cgt ctc tac gca aac tac ggc gtt gtg    1008
Lys Ala Phe Phe Arg Val Gly Arg Leu Tyr Ala Asn Tyr Gly Val Val
                325                 330                 335 gac cag gag gcg aag ctc ttc acg cta aag gaa gcc aag gcg gcg acc    1056
Asp Gln Glu Ala Lys Leu Phe Thr Leu Lys Glu Ala Lys Ala Ala Thr
        340                 345                 350 gag gcg gcg gcc aag acc aag tcc acg taa                            1086
Glu Ala Ala Ala Lys Thr Lys Ser Thr
                355                 360

<210> SEQ ID NO 10
<211> LENGTH: 361
<212> TYPE: PRT
<213> ORGANISM: Phytophthora infestans

<400> SEQUENCE: 10

Met Ala Thr Lys Glu Ala Tyr Val Phe Pro Thr Leu Thr Glu Ile Lys
1               5                   10                  15

Arg Ser Leu P

```
            50                  55                  60
Asp Ala Ala Leu Cys Thr Gly Tyr Ile Leu Leu Gln Gly Ile Val Phe
 65                  70                  75                  80

Trp Gly Phe Phe Thr Val Gly His Asp Ala Gly His Gly Ala Phe Ser
                 85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His
        115                 120                 125

Lys Asn Thr Gly Asn Ile Asp Arg Asp Glu Val Phe Tyr Pro Gln Arg
130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Ala Thr Ala Ala Phe
290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360

<210> SEQ ID NO 11
<211> LENGTH: 755
<212> TYPE: DNA
<213> ORGANISM: 35S-Virus
<220> FEATURE:
<221> NAME/KEY: promoter
<222> LOCATION: (1)..(755)

<400> SEQUENCE: 11
cctgcaggtc aacatggtgg agcacgacac acttgtctac tccaaaaata tcaaagatac      60
agtctcagaa gaccaaaggg caattgagac ttttcaacaa aggtaatat ccggaaacct     120 cctcggattc cattgcccag ctatctgtca ctttattgtg aagatagtgg aaaaggaagg    180
tggctcctac aaatgccatc attgcgataa aggaaaggcc atcgttgaag atgcctctgc    240
cgacagtggt cccaaagatg gacccccacc cacgaggagc atcgtggaaa aagaagacgt    300
```

```
                                          -continued tccaaccacg tcttcaaagc aagtggattg atgtgataac atggtggagc acgacacact      360
tgtctactcc aaaaatatca aagatacagt ctcagaagac caaagggcaa ttgagacttt      420
tcaacaaagg gtaatatccg gaaacctcct cggattccat tgcccagcta tctgtcactt      480
tattgtgaag atagtggaaa aggaaggtgg ctcctacaaa tgccatcatt gcgataaagg      540
aaaggccatc gttgaagatg cctctgccga cagtggtccc aaagatggac ccccacccac      600
gaggagcatc gtggaaaaag aagacgttcc aaccacgtct tcaaagcaag tggattgatg      660
tgatatctcc actgacgtaa gggatgacgc acaatcccac tatccttcgc aagacccttc      720
ctctatataa ggaagttcat ttcatttgga gagga                                 755

<210> SEQ ID NO 12
<211> LENGTH: 211
<212> TYPE: DNA
<213> ORGANISM: 35S-Virus
<220> FEATURE:
<221> NAME/KEY: terminator
<222> LOCATION: (1)..(211)

<400> SEQUENCE: 12
agtccgcaaa aatcaccagt ctctctctac aaatctatct ctctctattt ttctccagaa       60
taatgtgtga gtagttccca gataagggaa ttagggttct tatagggttt cgctcatgtg      120
ttgagcatat aagaaaccct tagtatgtat ttgtatttgt aaaatacttc tatcaataaa      180
atttctaatt cctaaaacca aaatccagtg a                                     211
```